United States Patent [19]

Shaw

[11] Patent Number: 5,431,639
[45] Date of Patent: Jul. 11, 1995

[54] TREATING WOUNDS CAUSED BY MEDICAL PROCEDURES

[75] Inventor: William J. Shaw, Cambridge, Mass.

[73] Assignee: Boston Scientific Corporation, Watertown, Mass.

[21] Appl. No.: 105,792

[22] Filed: Aug. 12, 1993

[51] Int. Cl.$^6$ .................... A61M 5/00; A61F 13/20; A61B 17/08; A61L 17/00
[52] U.S. Cl. .................... 604/264; 604/265; 604/11; 606/213; 606/229
[58] Field of Search .................... 604/11, 12, 265, 264; 606/213, 215, 216, 228–232

[56] References Cited

U.S. PATENT DOCUMENTS

| | | |
|---|---|---|
| 581,235 | 4/1897 | Kenyon . |
| 682,090 | 9/1901 | Lee . |
| 1,191,736 | 7/1916 | Roberson . |
| 1,794,221 | 2/1931 | Washburn et al. . |
| 1,879,249 | 9/1932 | Honsaker . |
| 2,396,351 | 3/1946 | Thompson .................... 128/2 |
| 2,603,217 | 7/1952 | McShirley .................... 128/239 |
| 2,691,373 | 10/1954 | Bried .................... 128/239 |
| 2,814,296 | 11/1957 | Everett .................... 128/339 |
| 2,898,913 | 8/1959 | Ritter et al. .................... 128/296 |
| 2,934,068 | 4/1960 | Graham, Jr. et al. .................... 128/263 |
| 3,056,408 | 10/1962 | Brown .................... 128/325 |
| 3,106,483 | 10/1963 | Kline et al. .................... 117/62.2 |
| 3,106,484 | 10/1963 | Miller .................... 117/62.2 |
| 3,358,684 | 12/1967 | Marshall .................... 128/214.4 |
| 3,396,727 | 8/1968 | Mount .................... 128/349 |
| 3,447,533 | 6/1969 | Spicer .................... 128/1 |
| 3,500,828 | 3/1970 | Podhora .................... 128/214.4 |
| 3,516,403 | 6/1970 | Cournut .................... 128/130 |
| 3,530,860 | 9/1970 | Majoros .................... 128/305 |
| 3,605,750 | 9/1971 | Sheridan et al. .................... 128/348 |
| 3,675,639 | 7/1972 | Cimber .................... 128/1 |
| 3,706,311 | 12/1972 | Kokx et al. .................... 128/285 |
| 3,736,939 | 6/1973 | Taylor .................... 128/349 |
| 3,739,778 | 6/1973 | Monestere, Jr. et al. .................... 128/214.4 |
| 3,833,003 | 9/1974 | Taricco .................... 128/347 |
| 3,858,571 | 1/1975 | Rudolph .................... 128/1 |
| 3,874,388 | 4/1975 | King et al. .................... 128/334 |
| 3,888,258 | 6/1975 | Akiyama .................... 128/305 |
| 3,941,127 | 3/1976 | Froning .................... 128/215 |
| 3,991,756 | 11/1976 | Synder .................... 128/214 |
| 4,007,743 | 2/1977 | Blake .................... 128/334 |
| 4,020,835 | 5/1977 | Nordstrom et al. .................... 128/214.4 |

(List continued on next page.)

FOREIGN PATENT DOCUMENTS

0019104A2 11/1980 European Pat. Off. .

(List continued on next page.)

OTHER PUBLICATIONS

Abbott et al., "Microcrystalline collagen as a topical hemostatic agent for vascular surgery," *Surgery*, vol. 75, No. 6, pp. 925–933, Jun., 1974.

Abbott et al., "The effectiveness and mechanism of collagen-induced topical hemostasis," *Surgery*, vol. 78, No. 6, pp. 723–729, Dec., 1975.

(List continued on next page.)

*Primary Examiner*—John D. Yasko
*Assistant Examiner*—Adam J. Cermak
*Attorney, Agent, or Firm*—Fish & Richardson

[57] ABSTRACT

Incised or injured tissue is treated by introducing material that encourages healing to desired depths within the tissue. Particularly, the invention provides treatment of an access channel to a blood vessel by introducing to the tissue a hemostatic material to a position that is located adjacent, but does not extend beyond, the vessel wall.

In one aspect, the invention features a device for treating an incision channel through tissue and the wall of a body lumen. The device includes a member having a proximal portion constructed to remain outside the body and an elongate generally tubular distal portion that is constructed to be introduced axially into the channel and be moveable axially therein. A detector is disposed on the side of the tubular distal portion. The detector is adapted to detect a predetermined condition indicative of an axial position within the channel. A healing promoting substance is carried by the member and releasable from the member into the channel at a desired axial location relative to the location indicated by the detector.

26 Claims, 17 Drawing Sheets

U.S. PATENT DOCUMENTS

| | | | |
|---|---|---|---|
| 4,030,504 | 6/1977 | Doyle | 128/325 |
| 4,114,618 | 9/1978 | Vargas | 128/214.4 |
| 4,154,226 | 5/1979 | Hennig et al. | 128/1 |
| 4,180,068 | 12/1979 | Jacobsen et al. | 128/214 |
| 4,182,339 | 1/1980 | Hardy, Jr. | 128/334 |
| 4,230,117 | 10/1980 | Anichkov | 128/303 |
| 4,306,563 | 12/1981 | Iwatschenko | 128/349 |
| 4,317,445 | 3/1982 | Robinson | 128/214.4 |
| 4,356,610 | 11/1982 | Hon et al. | 29/157 |
| 4,361,151 | 11/1982 | Fitzgerald | 128/285 |
| 4,390,018 | 6/1983 | Zukowski | 128/303 |
| 4,396,021 | 8/1983 | Baumgartner | 128/754 |
| 4,404,033 | 9/1983 | Steffan | 106/161 |
| 4,424,833 | 1/1984 | Spector et al. | 137/849 |
| 4,488,877 | 12/1984 | Klein et al. | 604/175 |
| 4,564,361 | 1/1986 | Akiyama | 604/265 |
| 4,577,631 | 3/1986 | Kreamer | 128/334 |
| 4,582,181 | 4/1986 | Samson | 128/348.1 |
| 4,587,969 | 5/1986 | Gillis | 128/334 |
| 4,588,395 | 5/1986 | Lemelson | 604/59 |
| 4,610,248 | 9/1986 | Rosenberg | 128/325 |
| 4,619,261 | 10/1986 | Guerriero | 128/325 |
| 4,645,488 | 2/1987 | Matukas | 604/59 |
| 4,650,488 | 3/1987 | Bays et al. | 623/12 |
| 4,655,211 | 4/1987 | Sakamoto et al. | 128/156 |
| 4,669,474 | 6/1987 | Barrows | 128/334 |
| 4,705,040 | 11/1987 | Mueller et al. | 128/334 |
| 4,708,147 | 11/1987 | Haaga | 128/753 |
| 4,710,181 | 12/1987 | Fuqua | 604/280 |
| 4,710,192 | 12/1987 | Liotta et al. | 623/1 |
| 4,744,364 | 5/1988 | Kensey | 128/334 |
| 4,774,091 | 9/1988 | Yamahira et al. | 424/426 |
| 4,790,819 | 12/1988 | Li et al. | 604/59 |
| 4,804,365 | 2/1989 | Litzie et al. | 604/4 |
| 4,827,940 | 5/1989 | Mayer et al. | 128/642 |
| 4,829,994 | 5/1989 | Kurth | 128/96.1 |
| 4,832,688 | 5/1989 | Sagae et al. | 604/53 |
| 4,836,204 | 6/1989 | Landymore et al. | 128/334 |
| 4,838,280 | 6/1989 | Haaga | 128/751 |
| 4,852,568 | 8/1989 | Kensey | 128/325 |
| 4,863,441 | 9/1989 | Lindsay et al. | 604/280 |
| 4,871,094 | 10/1989 | Gall et al. | 222/386 |
| 4,890,612 | 1/1990 | Kensey | 606/213 |
| 4,895,564 | 1/1990 | Farrell | 604/164 |
| 4,900,303 | 2/1990 | Lemelson | 604/54 |
| 4,929,246 | 5/1990 | Sinofsky | 606/8 |
| 4,936,835 | 6/1990 | Haaga | 604/265 |
| 4,958,625 | 9/1990 | Bates et al. | 128/754 |
| 4,976,726 | 12/1990 | Haverstock | 606/216 |
| 5,021,059 | 6/1991 | Kensey et al. | 606/213 |
| 5,041,124 | 8/1991 | Kensey | 606/170 |
| 5,042,984 | 8/1991 | Kensey et al. | 606/128 |
| 5,053,046 | 10/1991 | Janese | 606/215 |
| 5,061,274 | 10/1991 | Kensey | 606/213 |
| 5,061,281 | 10/1991 | Mares et al. | 623/11 |
| 5,062,829 | 11/1991 | Pryor et al. | 604/57 |
| 5,080,655 | 1/1992 | Haaga | 604/265 |
| 5,097,842 | 3/1992 | Bonn | 128/762 |
| 5,108,420 | 4/1992 | Marks | 606/213 |
| 5,108,421 | 4/1992 | Fowler | 606/213 |
| 5,120,299 | 6/1992 | Lombardi | 600/18 |
| 5,129,882 | 7/1992 | Weldon et al. | 604/96 |
| 5,147,315 | 9/1992 | Weber | 604/164 |
| 5,167,638 | 12/1992 | Felix et al. | 604/175 |
| 5,171,218 | 12/1992 | Fonger et al. | 604/164 |
| 5,178,611 | 1/1993 | Rosenberg | 604/172 |
| 5,185,001 | 2/1993 | Galanakis | 604/5 |
| 5,186,711 | 2/1993 | Epstein | 600/37 |
| 5,192,300 | 3/1993 | Fowler | 606/213 |
| 5,192,301 | 3/1993 | Kamiya et al. | 606/213 |
| 5,192,302 | 3/1993 | Kensey et al. | 606/213 |
| 5,195,988 | 3/1993 | Haaga | 604/265 |
| 5,219,895 | 6/1993 | Kelman et al. | 522/68 |
| 5,221,259 | 6/1993 | Weldon et al. | 604/96 |
| 5,222,939 | 6/1993 | Tiefenbrun et al. | 604/59 |
| 5,222,974 | 6/1993 | Kensey et al. | 606/213 |
| 5,254,097 | 10/1993 | Schock et al. | 604/167 |
| 5,254,105 | 10/1993 | Haaga | 604/265 |
| 5,263,969 | 11/1993 | Phillips | 606/213 |
| 5,275,616 | 1/1994 | Fowler | 606/213 |
| 5,282,827 | 2/1994 | Kensey et al. | 606/215 |
| 5,290,310 | 3/1994 | Makower et al. | 606/213 |
| 5,292,309 | 3/1994 | Van Tassel et al. | . |
| 5,292,332 | 3/1994 | Lee | . |
| 5,306,254 | 4/1994 | Nash et al. | . |
| 5,306,294 | 4/1994 | Winston et al. | 623/1 |
| 5,310,407 | 5/1994 | Casale | . |
| 5,312,435 | 5/1994 | Nash et al. | 606/213 |
| 5,320,639 | 6/1994 | Rudnick | . |
| 5,324,306 | 6/1994 | Makower et al. | . |
| 5,326,350 | 7/1994 | Li | . |
| 5,330,445 | 7/1994 | Haaga | 604/265 |
| 5,334,216 | 8/1994 | Vidal et al. | 606/213 |
| 5,342,393 | 8/1994 | Stack | 606/213 |
| 5,354,271 | 10/1994 | Voda | 604/49 |

FOREIGN PATENT DOCUMENTS

| | | |
|---|---|---|
| 0139091A1 | 5/1985 | European Pat. Off. . |
| 0210160A1 | 1/1987 | European Pat. Off. . |
| 0367516A1 | 5/1990 | European Pat. Off. . |

(List continued on next page.)

FOREIGN PATENT DOCUMENTS

| | | |
|---|---|---|
| 0476178A1 | 3/1992 | European Pat. Off. . |
| 0482350A2 | 4/1992 | European Pat. Off. . |
| 0522727A1 | 1/1993 | European Pat. Off. . |
| 2308346 | 11/1976 | France . |
| 2641692 | 7/1990 | France . |
| 3020611C2 | 12/1981 | Germany . |
| 782814 | 1/1977 | U.S.S.R. . |
| 737405 | 10/1977 | U.S.S.R. . |
| 1088709 | 2/1981 | U.S.S.R. . |
| WO89/11301 | 11/1989 | WIPO . |
| WO90/01497 | 2/1990 | WIPO . |
| WO90/14796 | 12/1990 | WIPO . |
| WO92/05740 | 4/1992 | WIPO . |
| WO92/19162 | 11/1992 | WIPO . |
| WO92/22252 | 12/1992 | WIPO . |
| WO93/01073 | 1/1993 | WIPO . |
| WO93/07813 | 4/1993 | WIPO . |
| WO93/08746 | 5/1993 | WIPO . |
| WO93/17731 | 9/1993 | WIPO . |
| PCT/US93/11864 | 6/1994 | WIPO . |
| PCT/US94/01337 | 8/1994 | WIPO . |

OTHER PUBLICATIONS

Allison et al., "Percutaneous Liver Biopsy and Track Embolization with Steel Coils," *Radiology*, vol. 169, No. 1, pp. 261–263, Oct., 1988.

Chuang et al., "Sheath Needle for Liver Biopsy in High-Risk Patients," *Radiology*, vol. 166, No. 1, pp. 261–262, Jan., 1988.

Chvapil et al., "A Standardized Animal Model for Evaluation of Hemostatic Effectiveness of Various Materials," *The Journal of Trauma*, vol. 23, No. 12, pp. 1042–1047, Dec., 1983.

Chvapil et al., "Experimental Experiences with the Collagen Sponge as Hemostaticum and Tampon," *J. Biomed. Mater. Res.*, vol. 2, pp. 245–264, 1968.

Chvapil et al., "Medical and Surgical Applications," pp. 1–61.

Gazelle et al., "Hemostatic Protein–Polymer Sheath: New Method to Enhance Hemostatsis at Percutaneous Biopsy," *Radiology*, vol. 175, No. 3, pp. 671–674, Jun., 1990.

Gazelle et al., "Hemostatic Protein Polymer Sheath: Improvement in Hemostasis at Percutaneous Biopsy in the Setting of Platelet Dysfunction," *Radiology*, vol. 187, No. 1, pp. 269–272, Apr., 1993.

Pfab et al., "Local Hemostasis of Nephrostomy Tract with Fibrin Adhesive Sealing in Percutaneous Nephrolithotomy," *Eur. Urol.*, vol. 13, pp. 118–121, 1987.

Richardson et al., "Peripheral Vascular Complications of Coronary Angioplasty," *The American Surgeon*, vol. 55, No. 11, pp. 675–680, Nov., 1989.

Riley et al., "Percutaneous Liver Biopsy With Plugging Of Needle Track: A Safe Method For Use In Patients With Impaired Coagulation," *The Lancet*, No. 8400, Aug. 25, 1984, pp. 436–438.

Silverstein et al., "Experimental and Clinical Experiences with Collagen Fleece as a Hemostatic Agent," *The Journal of Trauma*, vol. 21, No. 5, pp. 388–393, May, 1981.

Silverstein et al., "Collagen Fibers as a Fleece Hemostatic Agent," *The Journal of Trauma*, vol. 20, No. 8, pp. 688–694, Aug., 1980.

Takayasu et al., "A New Hemostatic Procedure for Percutaneous Transhepatic Portal Vein Catheterization," *Jpn. J. Clin. Oncol.*, vol. 18, pp. 227–230, 1988.

Tobin et al., "Plugged Liver Biopsy in Patients with Impaired Coagulation," *Digestive Diseases and Science*, vol. 34, No. 1, pp. 13–15, Jan., 1989.

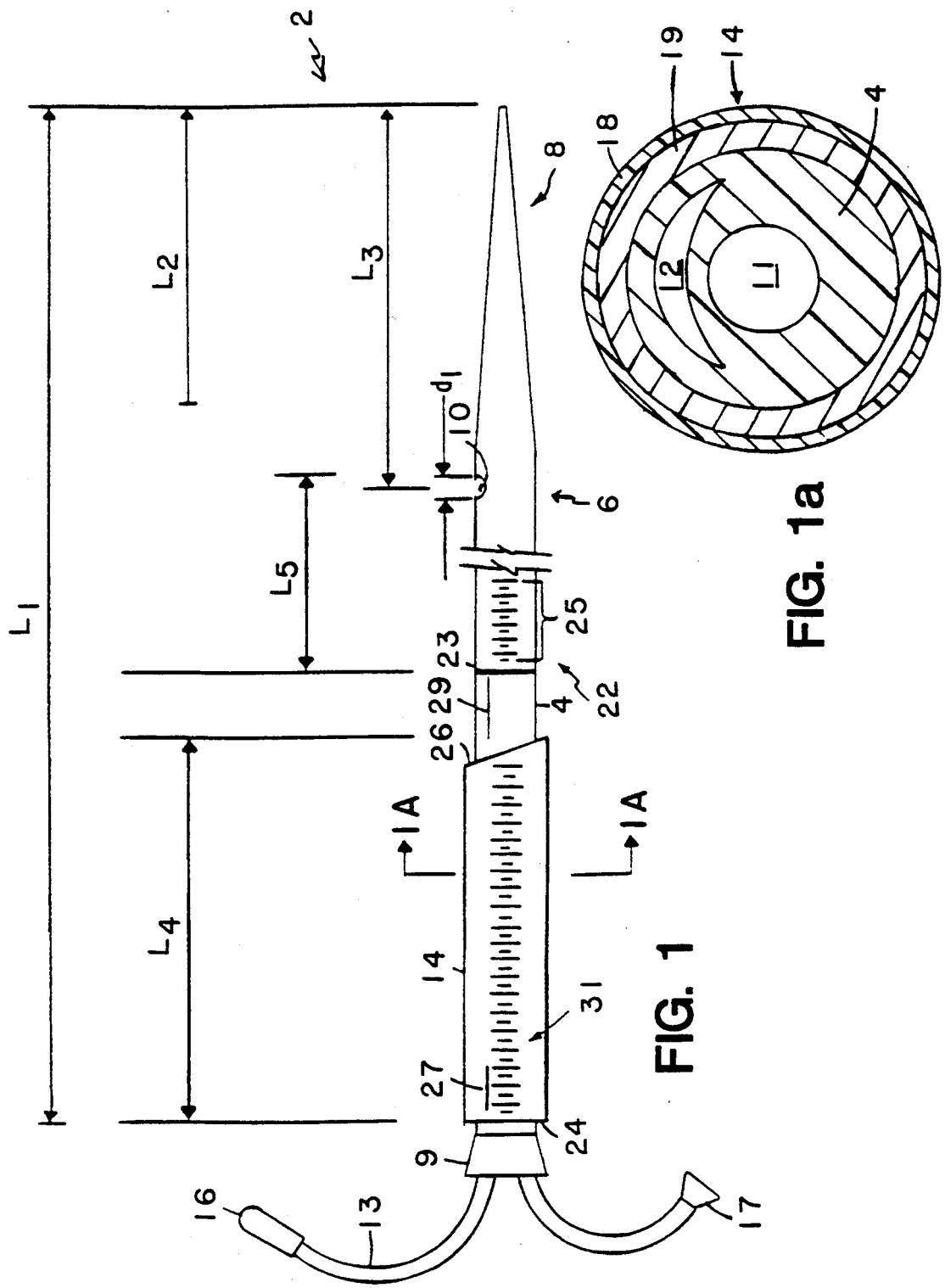

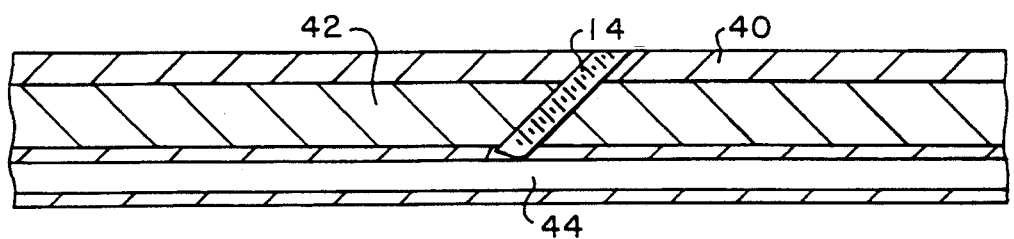
FIG. 2i
FIG. 8
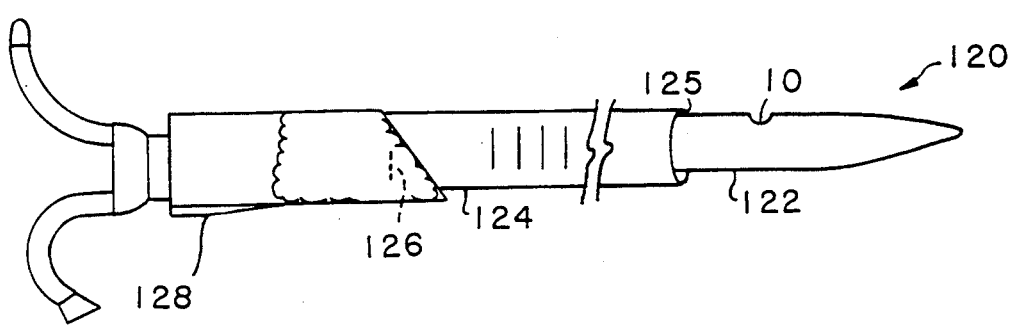

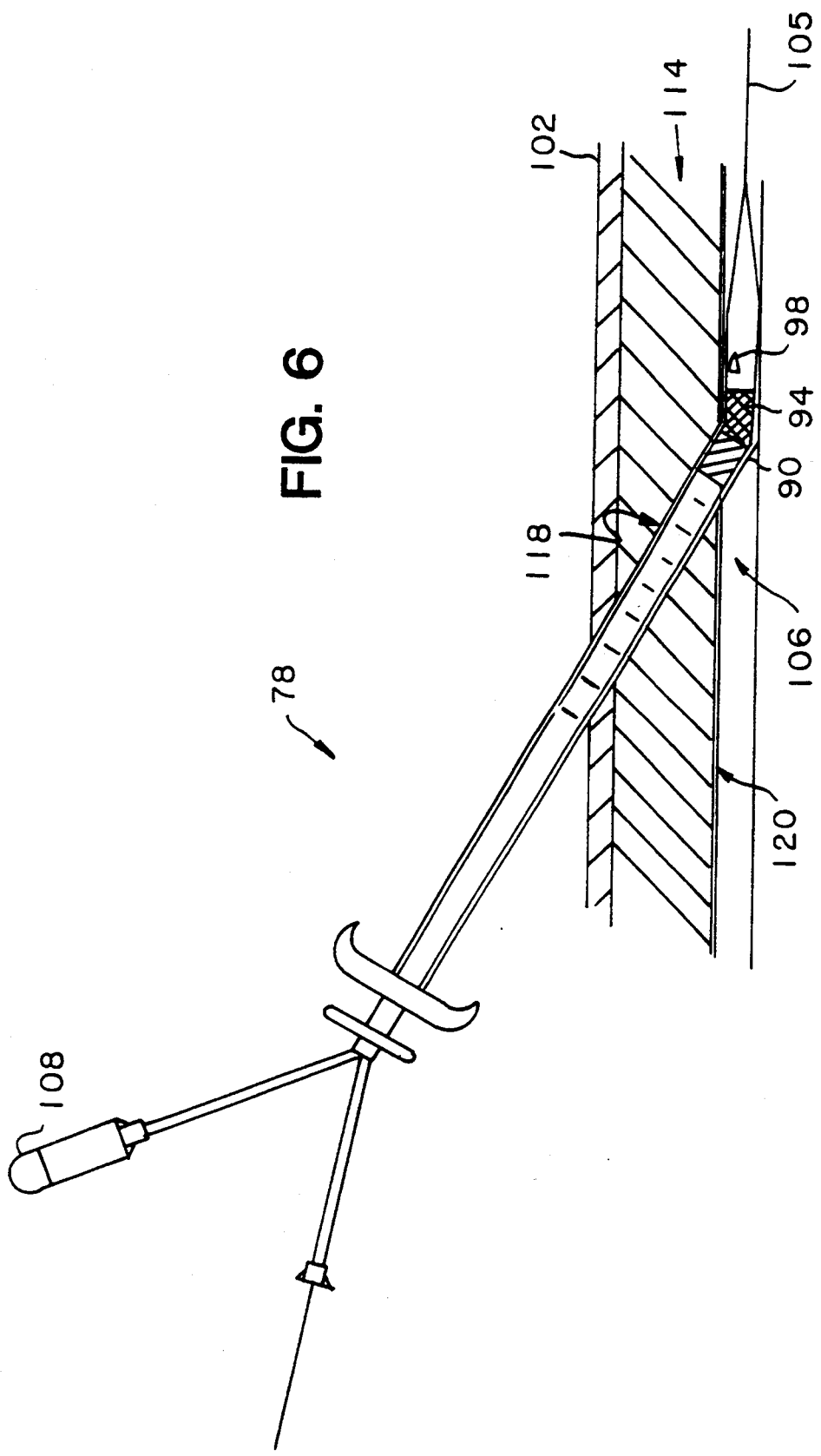

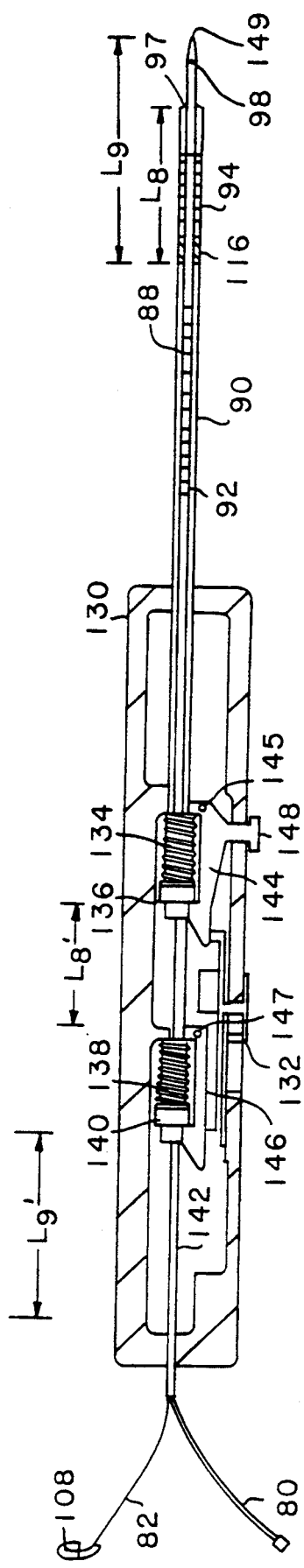

TREATING WOUNDS CAUSED BY MEDICAL PROCEDURES

FIELD OF THE INVENTION

This invention relates to treating wounds caused by medical procedures.

BACKGROUND OF THE INVENTION

In many medical procedures, a medical device must be placed in tissue that is well below the exposed surface of the body. Typically, an incision or puncture is made through surrounding tissue to gain access to the target tissue. After the procedure, the access incision is usually treated to encourage healing.

For example, in balloon angioplasty procedures, a narrow access channel is cut that extends from the body surface through the skin, the subcutaneous fascia (e.g. connective tissue, fat and muscle), and the wall of a blood vessel. An access catheter is placed in the access channel and the angioplasty catheter delivered into the vessel through the access catheter. At the end of the procedure, the access catheter is removed from the body. The access channel is treated by applying manual pressure to the site or depositing a hemostatic material into the channel to prevent excessive bleeding.

SUMMARY OF THE INVENTION

The invention provides treating incised or injured tissue by locating at desired depths within the tissue material that encourages healing. Particularly, the invention provides treating an access channel to a blood vessel by positioning a hemostatic material so that it is adjacent, but does not extend beyond the vessel wall into the vessel lumen.

In one aspect, the invention features a device for treating an incision channel through tissue and the wall of a body lumen. The device includes a member having a proximal portion constructed to remain outside the body and an elongate generally tubular distal portion that is constructed to be introduced axially into the channel and be moveable axially therein. A detector is disposed on the side of the tubular distal portion. The detector is adapted to detect a predetermined condition indicative of an axial position within the channel. A healing promoting substance is carried by the member and releasable from the member into the channel at a desired axial location relative to the location indicated by the detector.

Embodiments may include one or more of the following features. The detector is differentially responsive when exposed to the interior of the vessel and when exposed to the interior of the channel. The detector is sensitive to the flow of body fluid in the vessel. The detector includes a port in the wall of the generally tubular distal end portion so that the detector indicates when the port is exposed to the interior of the vessel by the flow of body fluid into the port and indicates when the port is exposed to the interior of the channel by the lack of flow of body fluid into the port. The port is in fluid communication with a lumen extending proximally to the proximal portion of the member outside of the body. The lumen is sealed distal of the port. The lumen extends proximally to a visual indicator so the flow of body fluid through the port is indicated visually by flow at the visual indicator. The detector is sensitive to the pressure in the vessel. The detector includes a pressure transducer. The detector is sensitive to the presence of chemical compounds. The detector is sensitive to the edge of the vessel wall during axial motion of the member. The detector is a portion of the wall of the member having regions of different diameter.

Embodiments may also include one or more of the following features. The device further includes a measuring system for measuring the depth of the channel to the position indicated by the detector. The measuring system includes a mark on the member with a known axial distance relationship to the detector. The substance for promoting healing has a proximal end, distal end, and a known length therebetween, and the substance is positionable by alignment with the mark to position the distal end at a known distance relationship with respect to the detector. The mark is located at a distance from the detector corresponding to the length of the substance so the distal end of the substance is adjacent the detector when the distal end of the substance is aligned with the mark. The measuring system includes a series of marks on the member of known distance from the detector for indicating the depth of the channel to the detector. The substance for promoting healing has a proximal end, distal end, and a known length therebetween and a series of marks indicating the distance from the distal end. The substance is slidably disposed on the exterior of the member. The substance is opaque, obscuring visual observation of portions of the member under the substance. The substance has a defined length greater than the depth of the access channel. The substance is axially moveable immediately after release from the member.

Embodiments may also include one or more of the following features. The healing promoting substance is carried on the outer exposed surface of the tubular distal portion and the device further includes a sheath positioned over the substance during entry into the channel and removable from the position over the substance for releasing of the substance in the channel. The sheath is an axially retractable sheath controllable from the proximal portion. The substance is a plug of hemostatic material with an axial length equal to or shorter than the depth of the channel. The plug is positioned proximally a known distance from the detector. The device includes a series of marks at least some of which are normally outside of the channel when the device is in use, the marks being spaced a known distance from the detector. The sheath includes a flexible seal-forming tip that extends distal of the plug during entry into the body and seals against the distal portion to prevent exposure of the plug to body fluid during entry into the body. The tip expands in diameter during retraction of the sheath over the plug. The tip seals against the distal portion at a proximal location after retraction of the sheath beyond the plug. The distal portion is removable to deposit the substance in the channel while leaving the sheath in the channel. The tip seals the sheath against the flow of body fluid after removal of the distal portion. The sheath is a thin-walled flexible sheath that can be collapsed by manual pressure after removal of the distal portion. The plug is held in a compressed form by the sheath when the sheath is positioned over the plug.

Embodiments may also include one or more of the following features. The substance for promoting healing is a body degradable substance. The substance is a hemostatic substance. The diameter of the distal portion is no greater at regions distal of the detector than at regions proximal of the detector. The distal portion includes a relatively flexible tip, distal of the detector, for positioning inside the vessel. The distal portion tapers distally to smaller diameter. The member includes a lumen for delivering the device to the channel over a guidewire.

In another aspect, the invention features a device for treating an incision channel through tissue and a blood vessel wall. The device includes a member having a proximal portion that remains outside the body and an elongate, general tubular distal end portion that is introduced into and axially moveable within the channel. A port is provided in the wall of the generally tubular end portion in fluid communication with a lumen that is sealed distal of the side port and extends proximally to the proximal portion of the member outside the body to a visual indicator. The flow of blood through the port and to the indicator indicates when the port is exposed to the vessel and the lack of flow of blood through the port to the indicator indicates that the port is exposed to the interior of the channel. A mark is provided on a portion of the member that remains outside the body having a known distance relationship to the port. A body-degradable hemostatic substance for promoting healing is carried by the member and releasable into the channel at a depth of known relationship to the mark.

Embodiments may include additional features mentioned above. Particular embodiments may include the following. The hemostatic substance has a proximal end, a distal end, and a known length therebetween greater than the depth of the channel. The substance is axially positionable by aligning the proximal end with the mark to position the distal end at a known distance relationship with the port. The mark is located at a distance from the port corresponding to the length of the substance for promoting healing. The device includes a series of marks of known distance from the port. The substance for promoting healing has a series of marks for indicating the length of the substance in the channel. The substance is slidably disposed on exterior of the member. The member includes a lumen for delivering the device to the channel over a guidewire. The diameter of the distal portion is no greater at regions distal of the detector than at regions proximal of the detector. The distal portion includes a relatively flexible tip, distal of the detector, for positioning inside the vessel.

In another aspect, the invention includes a device for measuring the length of an access channel through tissue and the wall of a vessel carrying body fluid under pressure. The device includes a member having a proximal end that remains outside the body and an elongate, generally tubular distal end portion that is introduced into and axially moveable within the channel. A detector is provided in the generally tubular distal portion for locating a position within the channel. A mark is provided on the proximal end of the member that remains outside the body, of known distance relationship to the port.

Embodiments may include additional features mentioned above. Particular embodiments may include the following. The detector is in fluid communication with a lumen extending to the proximal portion of the member outside the body and to a visual indicator so the flow of body fluid through the port is indicated visually by flow at the indicator. The port is a side port through the wall of the distal portion in fluid communication with a lumen sealed distal of the port.

In another aspect, the invention features a device for treating an incision channel through tissue and a blood vessel wall. The device includes a member having a proximal portion that remains outside the body and an elongate generally tubular distal portion that is introduced into the channel. A port is provided in the wall of the generally tubular distal portion in fluid communication with a lumen extending to the proximal portion. A body-degradable hemostatic substance for promoting healing is releasable from the member into the channel.

In these embodiments, the device may include features mentioned above. Particularly, the member may include a second lumen extending from the distal end of the distal portion to the proximal portion.

In another aspect, the invention features a device for treating an incision channel through tissue and the wall of a body lumen. The device includes a member having a proximal portion constructed to remain outside the body and an elongate generally tubular distal portion that is constructed to be introduced axially into the channel and be moveable axially therein. The device further includes a healing promoting substance that is carried by the member and releasable from the member into the channel at a desired axial location relative to the location indicated by the detector. The healing promoting substance is in the form of a tubular element having a length greater than the access channel. In particular embodiments, the tubular element may include marks indicating the distance to its distal end disposed inside the body.

In another aspect, the invention features a method for treating an incision channel through tissue and a vessel wall. The method includes providing a device as described above, introducing the tubular distal portion into the channel, extending the distal end portion axially distally until the detector indicates that the detector is within the vessel, retracting the distal portion axially proximally until the detector indicates that the detector is within the channel, the detector thus being located near the vessel wall, depositing the substance into the channel at a predetermined axial relationship with respect to the detector and, removing the device from the channel, leaving the substance in place.

In particular embodiments, the invention features iteratively moving the device axially proximally and distally to confirm the detector is located near the vessel wall, prior to depositing the substance. The method may include rotating the device about its axis to determine the radial variations of the channel or to determine the optimal orientation for detector response. The method may include providing a hemostatic substance having a desired length greater than the depth of the channel, so that a length of the substance is exposed above the channel, and moving the substance axially after removing the device by grasping the exposed length. The method may include removing the device substantially from the channel by withdrawing it axially. The method may include providing marks on the exposed length indicative of the length of substance positioned inside the channel and axially adjusting the length of substance inside the channel to extend to a desired depth. The method may include detaching, e.g., cutting, the exposed length of substance after the adjusting.

In other aspects, the invention features devices for positioning a plug of hemostatic material including mechanisms to automatically, sequentially retract a protective sheath from a position over the plug and a catheter carrying the plug to leave the plug at the proper location within the body.

In other aspects, the invention features clamping members to aid in locating a plug at the desired depth. These include clamping members having an additional function of cutting the plug to remove excess length after the plug has been properly positioned.

In one aspect, the invention features a device for treating an incision channel through tissue and the wall of a body lumen. The device includes a member having a proximal portion constructed to remain outside the body and an elongate generally tubular distal portion that is constructed to be introduced axially into the channel and be moveable axially therein. Healing promoting substance, carried by the member, is releasable from the member into the channel. The healing promoting substance, positioned over the member, is in the form of a tubular element and has a length greater than the access channel. A positioner, of cross-section greater than the diameter of the access channel, is axially fixable on the healing promoting substance at an axial distance from the distal end of the substance that corresponds to the depth of the channel to the desired location. The positioner and healing promoting substance are axially slidable to locate the portion of the substance distal of said positioner inside said channel so that the distal end of the substance is positioned at the desired location. The positioner prevents the portion of the substance proximal of the positioner from extending into the channel.

The advantages of the inventions are numerous. For example, axially positioning hemostatic material so that it is adjacent but does not extend beyond a blood vessel wall improves healing and reduces complications. If material is positioned too shallow in the access channel, such that it does not extend adjacent the vessel wall, blood can collect in the channel and cause a pseudoaneurysm, bruising or swelling. This condition can be very painful since the blood pressure in the vessel, e.g. the femoral artery, and, hence, the pseudoaneurysm, may be quite high. Blood under pressure in the channel may also push the material back out of the channel, which can cause bleeding. On the other hand, when material is positioned too deeply in an access channel, such that it extends beyond the vessel wall into the vessel lumen, the vessel can be occluded, reducing flow and increasing pressure. In addition, clots may form on the portions of the material in the vessel, raising the danger that clot material will be let loose into the bloodstream, causing an embolism. Moreover, aspects of the inventions feature the capability of manually pulling the material from the access channel should difficulties (e.g. vessel occlusion) become evident either during placement or even some period after placement. These aspects provide important advantages in safety and convenience, since the likelihood that mispositioned material will have to be surgically removed is reduced.

Further advantages and features follow.

BRIEF DESCRIPTION OF THE DRAWING

FIG. 1 is a side view of a device according to the invention for treating an access channel;

FIG. 1a is a cross-sectional view along the lines A-A in FIG. 1;

FIG. 7 is a cross-sectional view of an alternate embodiment of a device according to the invention;

FIG. 8 is a side view of an alternate embodiment of a device according to the invention;

DESCRIPTION OF THE PREFERRED EMBODIMENTS

Structure

Figure 1B:
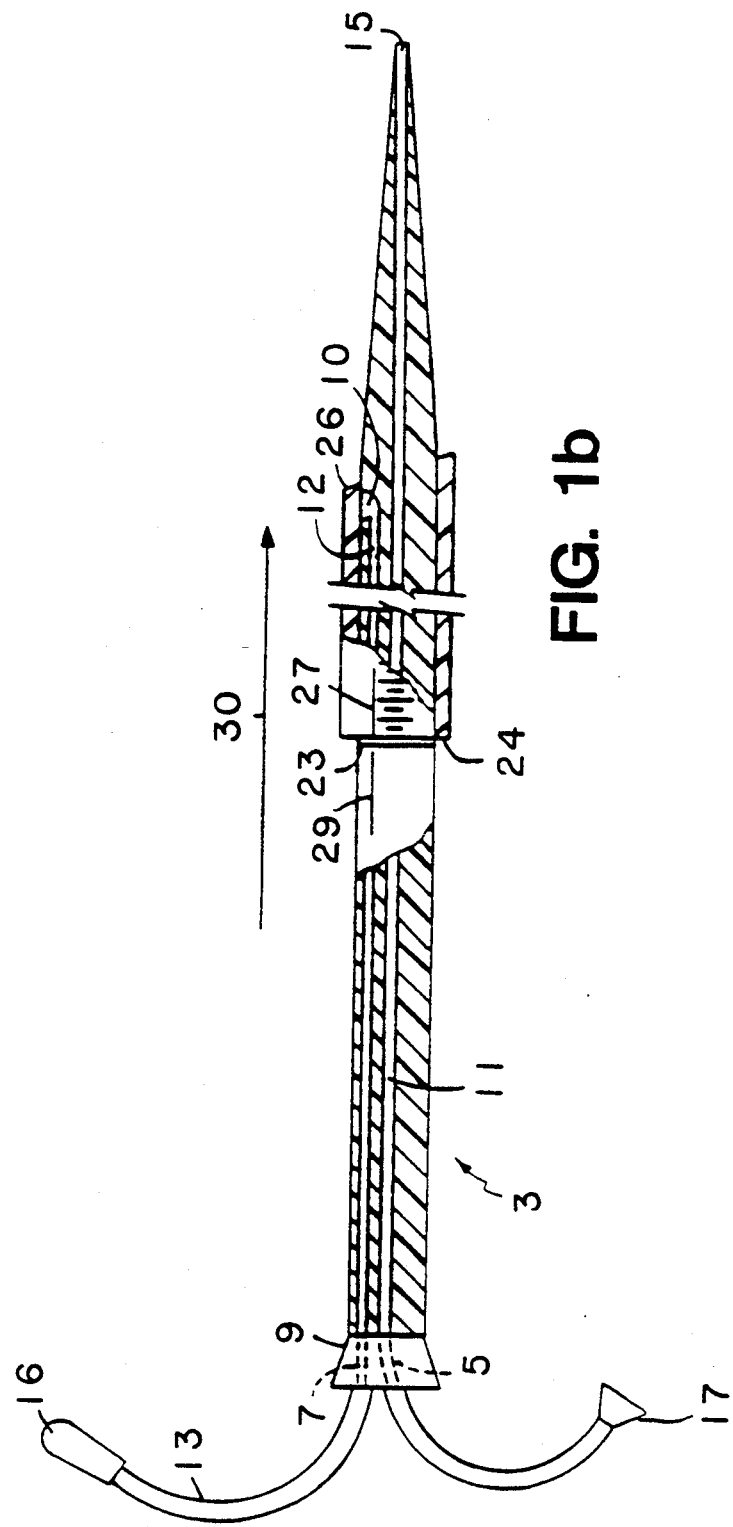
FIG. 1b is primarily a cross-sectional side view, with a partial side view, of the device in FIG. 1 with the treating material in an alternate location.

Referring to FIGS. 1-1b, a device 2 according to the invention is shown for treating an access channel to the femoral artery after a catheterization (e.g. angioplasty) or similar procedure. The device 2 includes a catheter body 4 with a side port 10 to an inner lumen 12. A long hemostatic plug 14 can be slid axially (arrow 30) along the catheter body. A depth indicating system 22 of marks can indicate the axial location of the distal end 26 of the plug relative to the port 10 when the distal end of the plug and the port are inside an access channel and out of view. When the port 10 is within an access channel, the tissue of the channel wall seals against the port, preventing blood flow through the lumen 12. When the port 10 is within the blood vessel, blood (which is at body pressures typically in the range of 120-200 mm Hg) flows through the port 10 into the channel 12. By detecting the flow of blood in the lumen 12 while moving the catheter body axially, the side port 10 can be axially located at a depth adjacent the vessel wall. Then, using the depth indicating system 22, the plug 14 is slid over the catheter body to position the distal end 26 of the plug so that it is adjacent the port 10 (FIG. 1b) and, hence, axially adjacent the vessel wall, but does not extend beyond the vessel wall into the vessel lumen. The catheter body is removed from the channel, leaving the plug 14 properly positioned in the channel.

The body 4, formed of a flexible, kink-resistant material such as nylon, has an overall length $L_1$, about 25 cm, which is substantially longer than the depth of an access channel to the femoral artery regardless of a patient's weight, age, and anatomical variations. The catheter body 4 has a proximal portion 3, an alignment portion 6, and a flexible distal guiding portion 8. The proximal portion 3 is relatively stiff, of substantially constant outer diameter (e.g. 8 French), and remains outside of the body. The alignment portion 6 includes depth indicating system 22 and port 10 and is also of substantially constant outer diameter (e.g. 8 French). The diameter of the alignment portion is similar to, e.g., slightly greater than, the width of the access channel, but is not so much greater to cause tearing or excessive stretching of the tissue forming the wall of the channel. The diameter is sufficient to prevent blood from leaking around the device and into the surrounding tissue. The proximal portion of the alignment portion, corresponding to the region near an end mark 23 of locating system 22, remains outside the access channel above the skin in use.

The relatively long flexible distal portion 8, of length, $L_2$, about 5 cm, tapers to an outer diameter of about 4.5 French or approximately one half the diameter of the alignment portion of the device. Most of the guiding portion 8 is disposed in the vessel in use. The taper makes the distal portion more flexible than proximal and alignment portions so that the distal portion will easily deflect when engaging a vessel wall to allow smooth axial motion when locating the side port adjacent the vessel wall. (In embodiments, the portion 8 (and distal portions of the alignment portion) may be made of a more flexible material than the stiffer pushable proximal portions proximal thereof.) The stiff, pushable, proximal portions and the taper in the distal portion facilitate dilation on entry into the channel.

The catheter body 4 has an internal guidewire lumen 11 (diameter about 0.040 inch), which extends from the proximal end to a distal end opening 15, allowing delivery of the catheter over a guidewire (about 0.038 inch). The guidewire lumen 11 communicates with a lumen 5 in a connector 9 to a guidewire control device 17, such as a Touhy-Borst valve.

The port 10, with a diameter, $d_1$, about 2 mm or less, e.g. about 1 mm, is positioned, $L_3$, about 5 cm, from the distal end of the body 4. The port 10 is a notch-cut in the catheter body that communicates with flow lumen 12. The flow lumen 12 is smile shaped to provide a large cross section (about 1.9 mm$^2$ for an 8F outer diameter body) without substantially sacrificing the strength of the catheter and its resistance to kinking. (Typically, the flow lumen cross-sectional area is about one-third the cross-sectional area of the catheter.) The flow lumen 12 has a sealed distal end so that it does not extend distally of the port 10. The flow lumen 12 extends proximally through the catheter body 4 to a lumen 7 in connector 9 that connects the flow lumen 12 with tubing 13, leading to an indicator 16. The indicator 16 is a clear plastic tube that provides a visual indication when port 10 is within the vessel, since blood flows through the port 10, lumen 12, tubing 13, and into the indicator 16. The indicator also provides a visual indication when the port 10 is located in the access channel, since blood will cease flowing in the indicator 16. (The indicator may be coupled to the tubing by a luer lock hub for easy aspiration of the lumen if desired.) Other indicator arrangements are possible. For example, the tubing 13 or polymer of at least portions of the body 4 may be clear, so blood flow can be seen.

The plug 14 includes a hemostatic material in annular form so that it can be slid axially (arrow 30) along the catheter body 4. The plug 14 includes distal end 26 which is bevelled to ease entry into the body and to match, roughly, the angle at which the access channel penetrates a vessel wall. (Alternatively, the distal end of the plug is tapered which also can aid entry into the channel.) The outer diameter of the plug 14 is selected based on the width of the access channel. For example, for an access channel previously occupied by a 9.5 French (outer diameter) access catheter (introducer), the plug 14, is between about 11-14 French (outer diameter). The inner diameter of the plug substantially corresponds to the outer diameter (8F) of the constant diameter portions of the catheter body 4.

The plug is of selected length, $L_4$, about 8 cm, which is longer than the expected depth of the femoral access channel so that a portion of the plug will extend beyond the skin when the distal end 26 of the plug is positioned adjacent the vessel wall. (The plug and, as mentioned, the catheter, can be made of sufficient length so the device can be used on all patients without regard to weight, age, etc.) In this manner, the plug can be easily slid distally over the catheter into the access site during insertion by manually grasping the exposed portion. Further, once the plug is positioned within the access channel, the exposed portion of the plug can be grasped and pulled to adjust its depth or remove it from the channel, if desired, even after the catheter body has been removed.

The plug, including portions that remain outside the body, and the alignment portion 6 of the catheter body 4 are constructed to allow accurate positioning of the distal end 26 of the plug once the side port 10 has been located adjacent the vessel wall. The alignment portion 6 of the catheter body includes depth indicating system 22 that indicates the distance to the side port 10. The system 22 includes an end mark 23, which marks the distance, $L_5$, about 8 cm, from the side port 10, corresponding to the axial length, $L_4$, of the plug 14. Referring particularly to the non-sectional side view portion of FIG. 1b, when the proximal end 24 of the plug 14 is aligned with the end mark 23, the distal end 26 of the plug 14 is positioned adjacent the side port 10, with the side port positioned adjacent the vessel wall, the distal end 26 of the plug can be located adjacent the vessel wall without measuring the actual depth of the channel.

The depth indicating system 22 also includes a series of additional marks 25 running distally that are known distances from the side port 10. The marks 25, which may be numbered to indicate actual distance (numbers not shown), can be used to measure the actual depth of the access channel by noting the mark adjacent the surface of the skin when the port is located adjacent the vessel wall. In addition, the plug also includes graduated marks 31 that indicate the distance from the distal end 26 of the plug 14. The marks 31 can be used to accurately position the plug 14 in the access channel by aligning with the skin surface the mark on the plug that corresponds to the depth of the access channel that was measured using the marks 25 on the catheter. In this arrangement, the plug 14 can be slid over the catheter body 4 and accurately positioned without the need to accurately maintain the axial position of the plug or catheter in the access channel. The marks 31 on the plug are particularly useful when the plug is formed of an opaque material that obscures marks on the catheter once the plug is slid distally. The plug 14 also includes an axially oriented alignment mark 27 and catheter body 4 includes a corresponding mark 29. By aligning these marks, the rotational orientation of the bevel on the distal end 26 of the plug 14 can be selected. Mark 29 also is indicative of the rotational orientation of side port 10. The marks on the catheter and plug can be made by application of ink, laser radiation, etc.

Referring particularly to FIG. 1a, the plug 14 is preferably formed of a biodegradable material so that it need not be removed surgically after the access channel has healed. The plug includes an inner layer 19 of soft bovine collagen (about 0.3-0.5 mm thick) and an outer layer 18 of a stiffer material. The soft collagen, of a type formed as a freeze-dried dispersion, rapidly absorbs blood cells and facilitates the body's natural healing process by providing a surface for fibrin and clot formation. The hemostatic material swells to fill the internal lumen and block off the access site after the catheter body is removed. The stiffer material may be, for example, plastic, gelatin, or, particularly, a stiffer, nonporous collagenous material (for example, 0.3-0.5 mm thick), of the type formed by dipping into a collagen solution. The stiffer material supports the softer, spongy inner material and provides a firm gripping surface so that the plug can be easily slid axially along the catheter body 4. The stiffer outer layer 18 is kept thin so as not to inhibit movement or cause discomfort in the patient. In the case of a stiff collagenous outer layer, collagen may be selected which softens quickly, e.g. in about 15 seconds after exposure to tissue. This material also swells slightly and presses against the inner wall of the channel, which helps anchor the plug, although anchoring is primarily achieved by fibrin that bridges across the plug and adjacent the vessel wall. Both the inner 19 and outer layer 18 degrade within the body. A thin coating (not shown) of gelatin may be placed at the interface between the two layers to provide adhesion. A lubricant, for example a hydrogel or silicone, may be placed on the catheter body and, likewise, on the exterior surface of the outer layer 18 to reduce friction when sliding the plug into the body. The plug may have mechanical or pharmaceutical properties selected for a particular application and may contain materials other than collagen. Plugs of the types described herein are available from Integra, Plainsborough, N. J. Hemostatic plugs are also described in U.S. patent application Ser. No. 787,518 by J. R. Haaga, filed Nov. 4, 1991, and U.S. Pat. No. 4,838,280. The entire contents of both of these cases are hereby incorporated by reference.

Use

Figure 2:
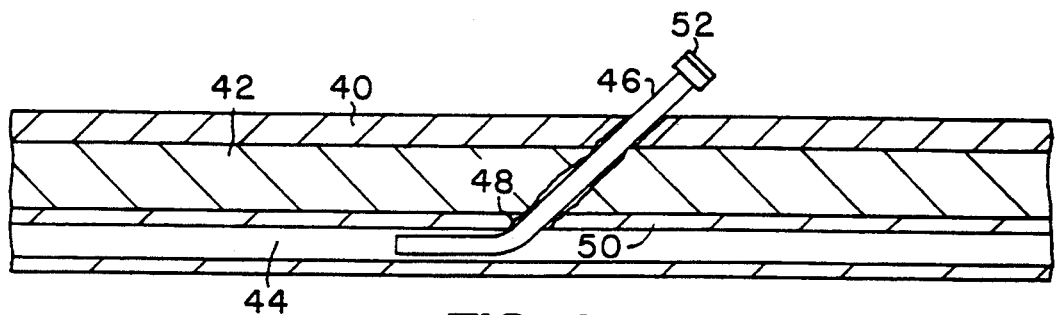
FIGS. 2-2i illustrate use of the device in FIG. 1.

Referring to FIGS. 2-2i, an access channel may be treated using a device as described in FIG. 1, as follows. An access channel is formed by making an incision with a thin needle that punctures the tissue, then widening the puncture using dilators. The channel, therefore, is characterized as a rip or tear of the tissue. The walls of the incision rebound to fill the incision opening unless a device such as a catheter is provided in the incision to push the walls outwardly. Referring particularly to FIG. 2, in a typical operation where access is needed to the femoral artery 44, an introducer catheter 46 (e.g. 2-3.5 mm in diameter) is positioned in an access channel 48 through tissue, including skin 40 (usually about 0.25 inch thick), underlying fascia 42 (usually about 1-2 inch thick) and the wall 50 (usually about 1 mm thick) of the artery (about 6-10 mm lumen diameter). During the operation, the access catheter 46 is used to introduce diagnostic or therapeutic catheters, e.g. angioplasty balloon catheters. A valve 52 can be opened to deliver these medical devices. Before the operation, anticoagulants may be delivered through the access catheter 46 to inhibit clot formation in the artery. After the operation, the access catheter is left in the body for a few hours until the anticoagulant has been taken up systemically.

Figure 2A:
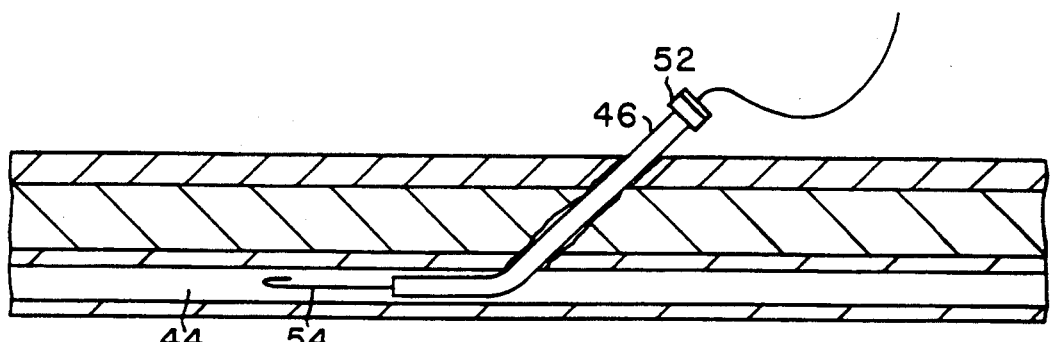

Referring particularly to FIG. 2a, to treat the access channel after the operation, a guidewire 54 (0.038 inch) is passed through the access catheter 46 and into artery 44. The guidewire may be 80 cm in length, generally longer than the delivery device by about 40 cm, and includes a J-tip to avoid puncturing the vessel wall.

Figure 2B:
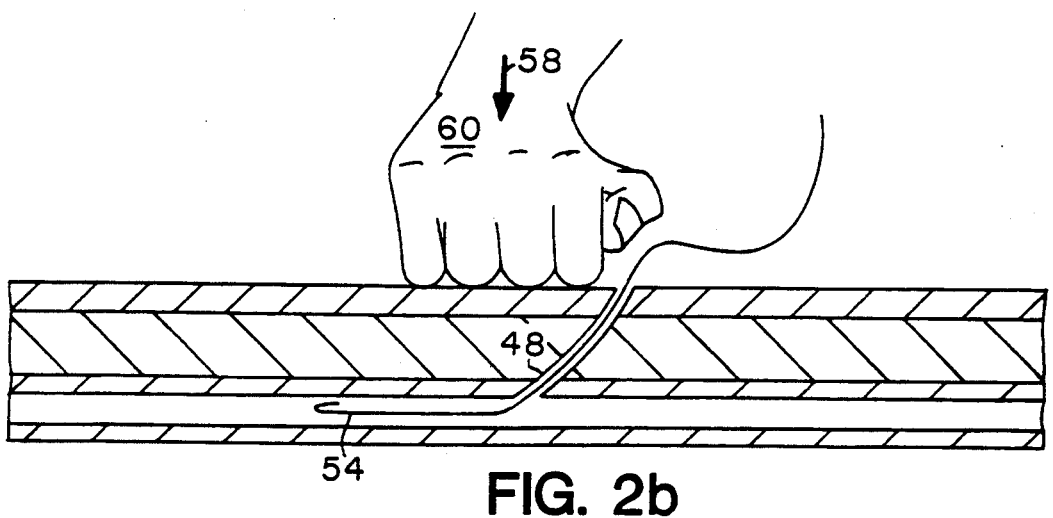

Referring to FIG. 2b, the access catheter is then removed from the access channel 48, leaving the guidewire 54 in place. The tissue that makes up the wall of the access channel which is an incision or puncture, fills in around the guidewire once the access catheter has been removed. (Although, for clarity, the access channel is shown in FIG. 2b as an open lumen.) Yet, significant bleeding can occur through the channel if manual compression (arrow 58), by, for example, the physician's hand 60 is not applied, since blood under pressure can open the channel.

Figure 2C:
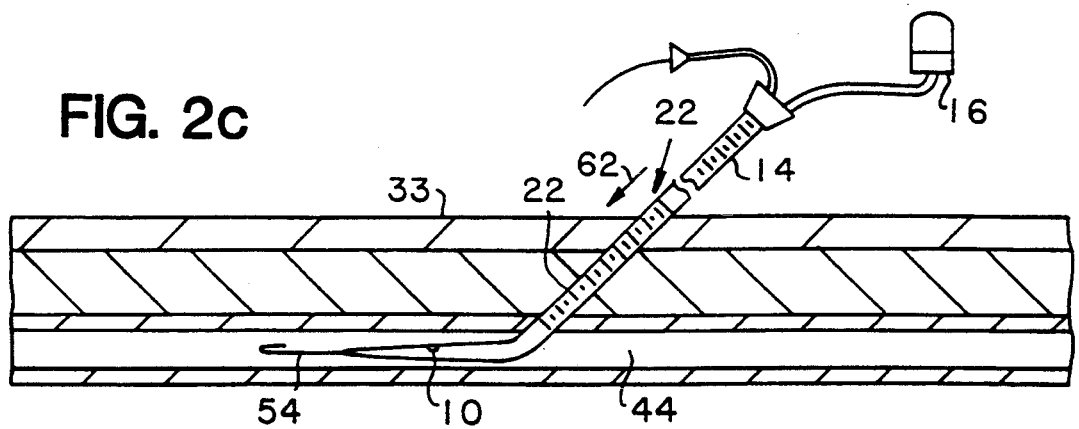

Referring to FIG. 2c, the device 2 is positioned over the guidewire 54, with the plug 14 initially over the proximal portion remaining outside the body. The alignment portion 6 is primarily located within the body, with at least a portion of the depth indicating system 22 visible above the surface 33 of skin 40. As illustrated, the device 2 is initially positioned such that the port 10 is within the artery 44. Although the physician cannot, of course, see the distal end of the catheter, its location within the artery is indicated by blood flow in the indicator 16, which was delivered through the port 10 and through the flow lumen 12. The catheter may also be rotated while in the blood vessel, to assure that the side port is not pressed against and occluded by the wall, giving a false indication that the port is in the access channel.

Figure 2D:
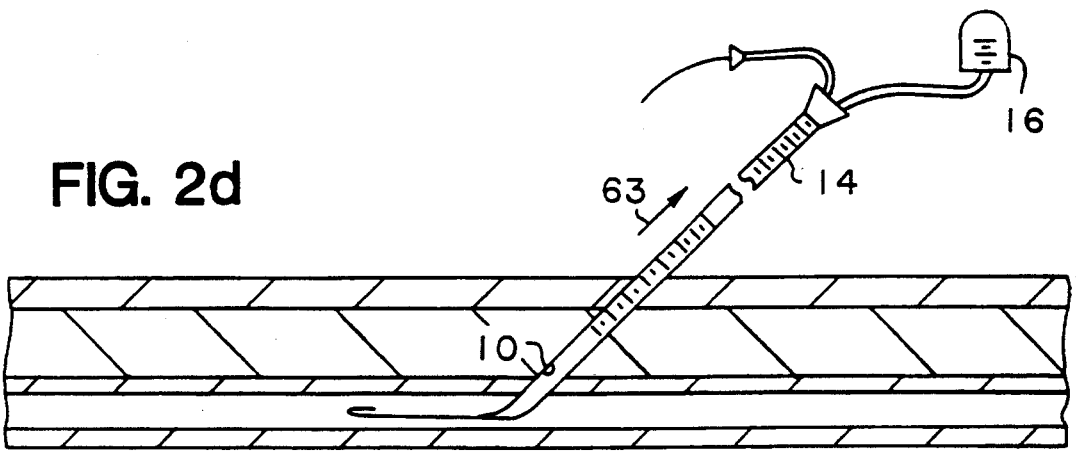

Referring to FIG. 2d, the catheter device 2 is moved proximally (arrow 63) until the port 10 is located within the access channel. The wall of the access channel seals against the port and prevents the flow of blood through it. This condition is visually indicated by the cessation of blood flow in the indicator 16.

Figure 2E:
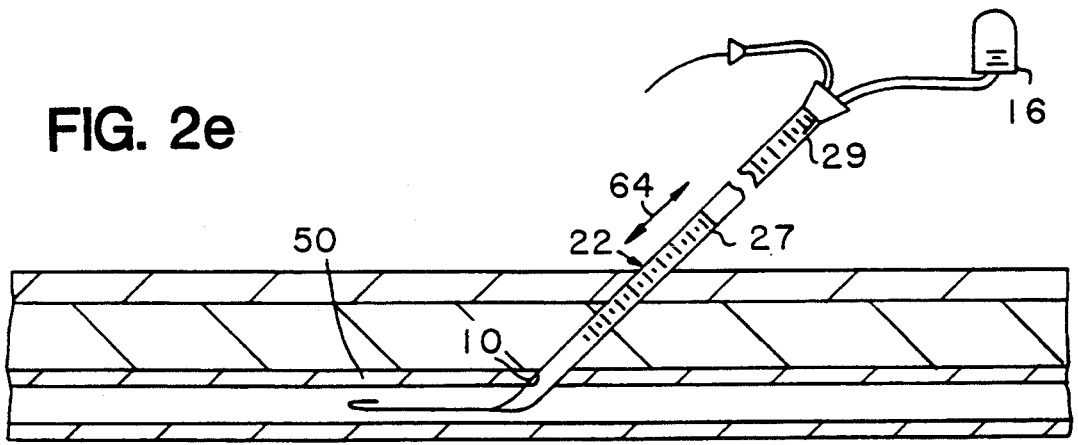

Referring to FIG. 2e, the device 2 is iteratively moved axially (arrow 64) to accurately locate the side port 10 at a depth adjacent the wall 50 of the artery 44, by observing the flow of blood and lack thereof, in the indicator 16. While not necessary in all cases, the device body may also be rotated about its axis to rotationally orient the catheter so the distal end of the plug can in turn be rotationally oriented to conform to the shape of the opening in the vessel wall. For example, when the access channel is at an angle with respect to the vessel wall and a plug with a beveled distal end is used to match the angular shape of the opening at the vessel wall, it is desirable to first orient the side port, as shown, so that any rotation of the catheter about its axis will position the side port deeper within the body. This rotational orientation may be confirmed by rotating the catheter and observing blood flow. If the port is properly oriented, as rotation begins, blood flow will increase until the body is rotated to a position 180° from the initial position, since at that point the port is positioned at the greatest depth and becomes maximally exposed to the flow in the vessel. As rotation continues beyond the 180° point from the initial position, there is a gradual decrease in flow. With the catheter in this rotational orientation, the plug can be oriented (by alignment of marks 29 and 27) so the beveled shape of the distal end of the plug conforms with the vessel wall so the distal end of the plug is flush with the vessel wall. Rotation of the catheter body can also determine irregularities of the shape opening in the vessel wall, such as torn or stretched portions, that can be taken into account by the physician in positioning hemostatic material. The physician may also shape the distal end of the plug to conform to the irregularities.

Figure 2F:
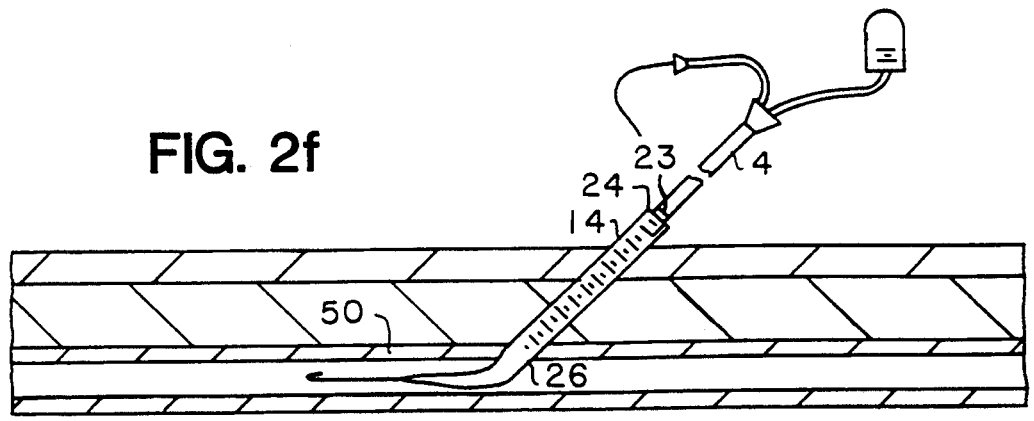

Referring to FIG. 2f, with the device 2 positioned such that the side port 10 is located adjacent the vessel wall 50, the hemostatic plug is slid axially into the access channel and the proximal end 24 of the plug is aligned with the end mark 23 of depth indicating system 22. In this position, the distal end 26 of the plug 14 is located adjacent the side port 10, which is, as mentioned, adjacent the side wall 50. The plug may be accurately positioned such that the distal end is not substantially proximal of the superior surface of the vessel wall.

As noted above, the plug 14 includes graduated marks 31 and the catheter depth indicating system 22 includes graduated marks 25 in addition to the end mark 23. When the port 10 is located adjacent the vessel wall, the number of graduated marks on the catheter above the skin (or the depth reading of the particular mark adjacent the skin) is noted by the physician to measure the depth of the access channel. While advancing the plug 14, the axial position of catheter body 4 need not be maintained. The plug 14 may be properly positioned with its distal end adjacent the vessel wall by noting the marks 31 on the plug so that the depth of the plug in the channel corresponds to the depth of the channel previously measured by the use of the marks 25. If the plug is formed of a transparent material, no additional marks may be provided on the plug 14, since the marks 25 can be easily viewed through the plug to confirm that the catheter is at the proper depth, with the port 10, adjacent the vessel wall.

Figure 2G:
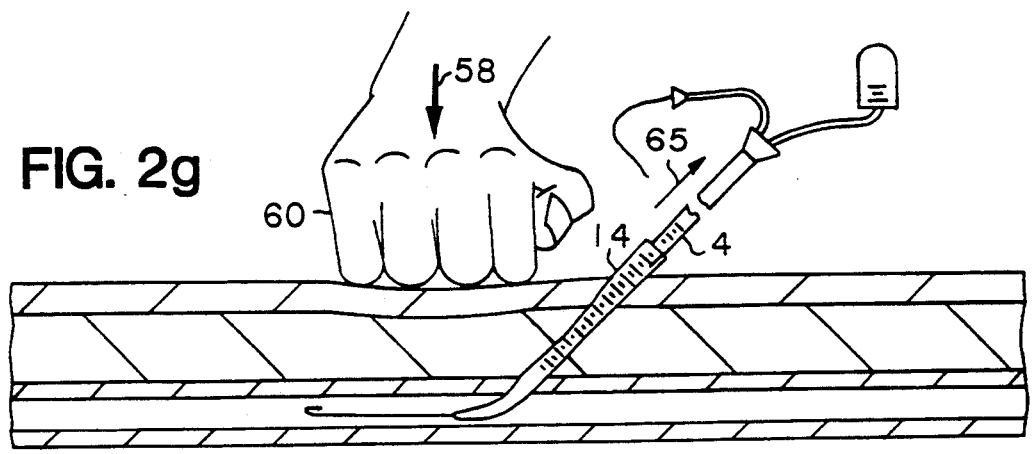

Referring to FIG. 2g, after accurately positioning the distal end of the plug 14 adjacent the vessel wall, the catheter 4 is removed from the access channel by drawing it axially distally (arrow 65), while maintaining manual compression (arrow 58, hand 60). The guidewire may be removed before or after the catheter. An advantage of the system is that, by maintaining the guidewire in the body throughout most of the operation, the device can be easily removed and replaced if it becomes desirable. The additional marks 31 on the plug can be used to confirm that the plug is at the proper depth, even after the catheter has been removed.

Figure 2H:
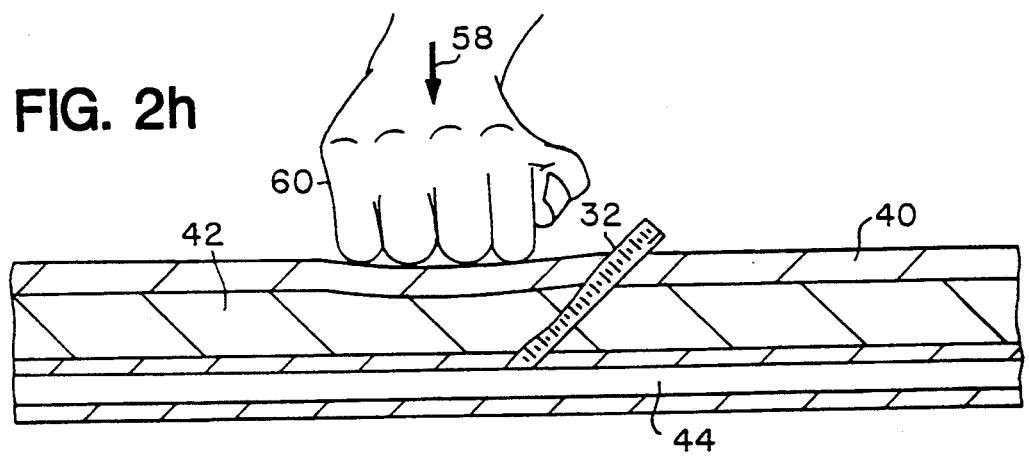

Referring to FIG. 2h, with the catheter 4 completely removed, a proximal portion 32 of the plug 14 still extends out of the access channel. As mentioned, the overall length of the plug 14 is selected to be greater than the length of the access channel, which may vary depending on the age, weight, etc. of the patient. The portion 32 of the plug extending beyond the skin provides for accurate manual positioning of the plug in the channel, as discussed above, and also provides a safety feature once the plug has been located and the catheter removed. Should it be the case that the distal end of the plug has been improperly positioned, for example, such that it extends into the artery 44, the plug can be removed from the access channel without surgery, by pulling proximally on the exposed portion 32. Typically, using a two layer plug as discussed above, the protective plug can be removed up to 3 hours after implantation, a time after which the portions of the protective plug within the body degrade beyond the point which they can be removed as a unit by pulling axially on the exposed portion 32. The effective removal time can be varied by using different types of materials in the plug.

Referring to FIG. 2i, after the waiting period to ensure that there are no complications, the portion 32 of the protective plug extending beyond the skin is cut off with forceps. The portions of the protective plug remaining in the channel degrade over time and need not be removed.

Other Embodiments

Figure 3:
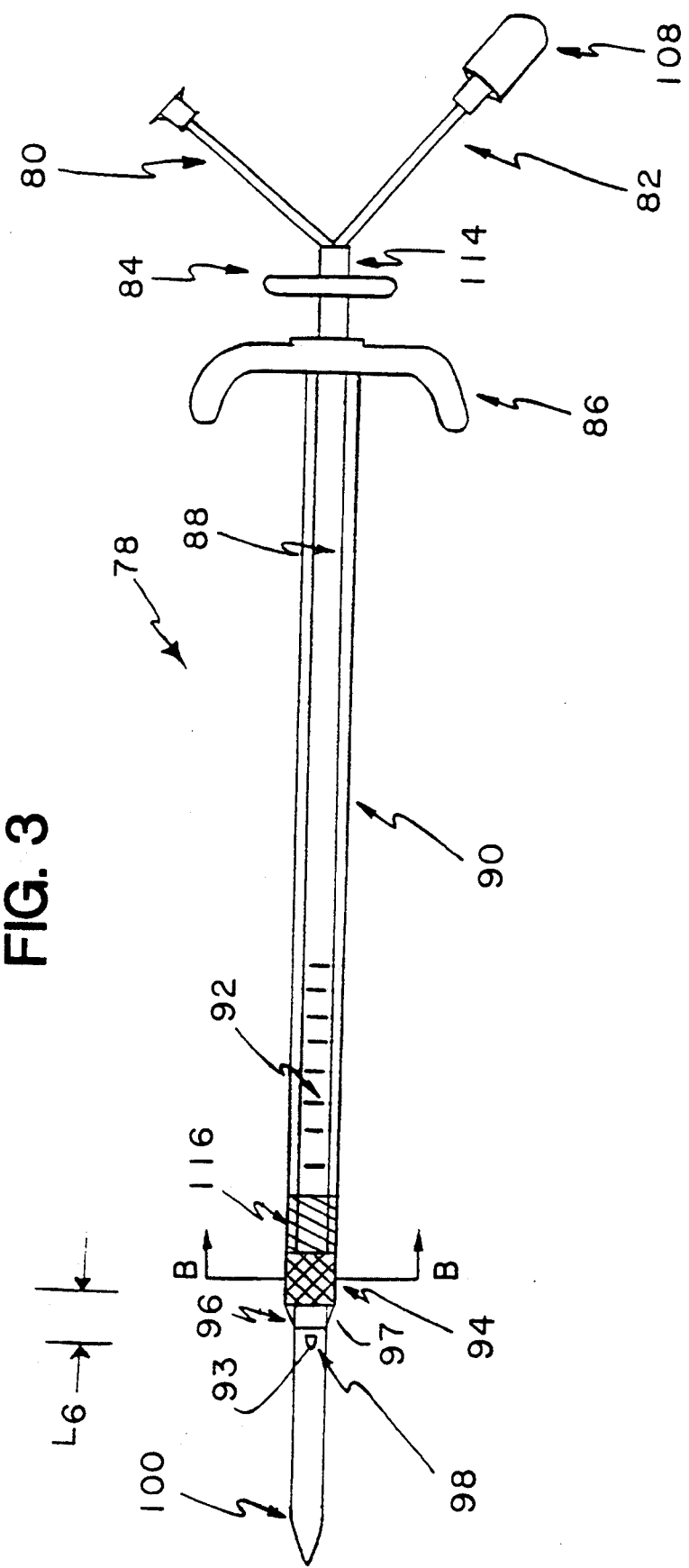
FIG. 3 is a side view of an alternate embodiment of a device according to the invention.
Figure 3A:
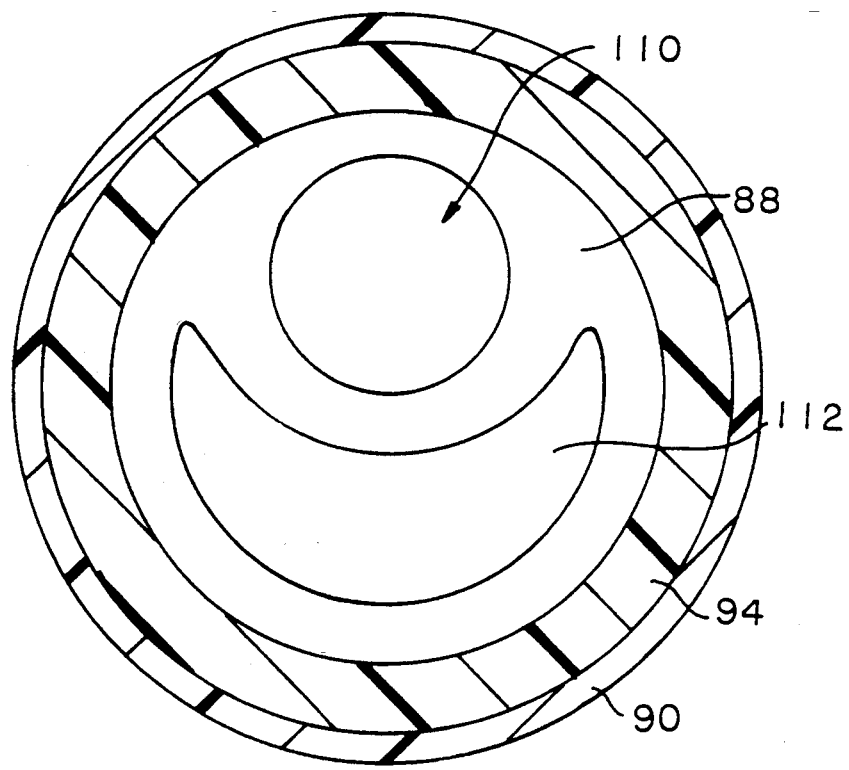
FIG. 3a is a cross-sectional view along the lines B-B in FIG. 3.

Referring to FIGS. 3-3a, a delivery device 78 is illustrated which uses a side port vessel wall locating system, but does not require sliding a hemostatic plug over the catheter body during positioning. The devices allow a one step delivery of a hemostatic material at a desired location in the access channel. The embodiment includes a catheter 88 with a side port 98 to an inner lumen 112, a series of marks 92 indicating depth from the side port, a short annular plug 94 of hemostatic material positioned adjacent the side port, and a protective sheath 90. In FIG. 3, the device is configured for entry into the body and positioning using the side port, with the sheath 90 positioned over the plug 94. After the side port is positioned adjacent the vessel wall, the catheter is advanced axially distally the known distance, $L_6$, from the port to the distal end of the plug, using the marks 92, to accurately position the plug adjacent the wall of the vessel. The sheath is retracted to expose the plug to the access channel. The sheath may be retracted so its distal end is adjacent the proximal end of the plug. The catheter can be withdrawn, with the sheath preventing axial distal movement of the plug. The sheath can be removed thereafter.

Catheter 88 is a two lumen polymer extrusion of a material such as nylon that exhibits good flexibility, kink resistance, antithrombogenicity, maneuverability and workability (in fabrication). Referring particularly to FIG. 3a, catheter 88, of outer diameter 8 French (may be specific to the arteriotomy size), has guidewire lumen 110 and smile shaped lumen 112. Guidewire lumen 110 is typically 0.038 inch in diameter or greater. The lumen 112 has an almost semi-circular shape with a diameter that may be close to twice that of the lumen 110, e.g., 0.070 inch. The cross-sectional area is about 0.0019 inch$^2$ (1.236 mm$^2$) (about one-third the cross-sectional area of the delivery device) for the lumen 112 and 0.0011 inch$^2$ (0.710 mm$^2$) for the guidewire lumen 110. The sizes of these lumen are selected based upon the diameter of catheter 88, maximizing blood flow, and allowing easy maneuverability over a guidewire. The catheter 88 has two proximal hubs, 80 and 82, attached to the lumens. Each hub has a luer lock fitting and an extruded polymer tube, 5-8 cm long. The hubs 80 and 82 are joined to the catheter 88 at a connector 114. The connector is injection molded or glued to the catheter to ensure a tight seal. Hub 80 is connected to the lumen 110 and is sized 0.038 inch to accept the guidewire. Hub 82 is connected to the side port lumen 112 and allows blood flow through the side port to reach the blood flow indicator 108. Indicator 108 is a clear or translucent sealed chamber made of a material such as polycarbonate. It serves to allow visual confirmation of blood flow while avoiding blood exposure or loss.

Catheter 88 is typically 25 cm long from the bottom of a handle stop 84 to the tip of distal guiding portion 100. Distal portion 100 is tapered to allow easy entry to the puncture access site. Portion 100 may be made of a softer material than the rest of the catheter to reduce the likelihood of tissue or vessel injury upon insertion. Typically, the side port 98 is about 5 cm from the distal tip of catheter 88 and is located 20 cm from the proximal end of catheter 88. The side port 98 is a triangular skive over lumen 112 with a base of about 1 mm and a height of 1-2 mm. The size of side port 98 is selected to allow sufficient blood flow while not allowing for erroneous readings of flow by being too sensitive when outside the body vessel or duct.

Catheter 88 further includes depth marks 92 located from the side port 98, proximally. These marks 92 are fabricated in a manner such as ink imprintation or laser burning and are located, e.g., at every 0.5 cm proximal from the side port 98 up to 10 cm proximal to the side port 98. (Finer graduations may be used to more accurately measure depth.) Marks 92 are preferably located around the circumference of the catheter 88 and may be numbered and/or indicated with a variety of colors to help associate color with depth.

Just below the connector 114 is handle stop 84 that prevents removal of the protective sheath 90 from the catheter 88 without first removal of the catheter. The handle stop 84 stops syringe handles 86 which are connected to the sheath 90. The curved shape of the handles 84 indicates their use by pulling rather than pushing protective sheath 90. (This indication may also be given by providing ringlets.)

The handle 86 controls axial positioning of protective sheath 90. Protective sheath 90 is made of a clear, flexible polymer material such as polyethylene. The clear material allows visual observation of the marks 92 on the catheter 88. (If a clear material is not used for the sheath, depth marks can be provided on the outside of the sheath.) Protective sheath 90 is typically thin, 0.010 inch, and made of an extruded tube which is 4–6 French (1–2 mm) larger in outer diameter than catheter 88 outer diameter. The thin sheath 90 is flexible, kink resistant and readily collapsible under manual pressure. The inner diameter of protective sheath 90, in accordance with the thickness, is 2–4 French (0.7–1.3 mm) greater than the outer diameter of catheter 88. Protective sheath 90 is typically 17 cm long and, in the position for entry into the body, the tip 96 is proximal to the side port 98. The distal tip 96 of protective sheath 90 tapers to the outer diameter of catheter 88. The tip 96 seals against the catheter to prevent body fluid from reaching the plug during tissue entry. The tip 96 opens up over the plug 94 during protective sheath pullback. There is a gap of about 2 cm between the handle 86 of the protective sheath and the handle stop 84 of the catheter. This distance between the handle 86 and the handle stop 84 is dependent upon the length of (hemostatic) plug 94. In full retraction, the distal end of the tip seats just proximal of the plug. The tip 96 reseals onto catheter proximally to plug 94 to support the plug 94 to inhibit it from being pulled proximally when the catheter is withdrawn from within the protective sheath 90. After the catheter is withdrawn, the tip 96 seals the sheath opening to prevent blood flow while the hemostatic material promotes clot formation. The sheath can thereafter be removed.

Figure 4:
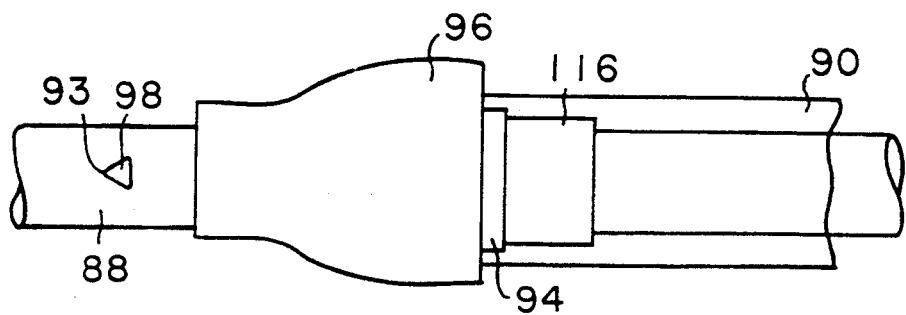
FIGS. 4-4b show a tip for a protective sheath for use with the embodiment of FIG. 3.
Figure 4A:
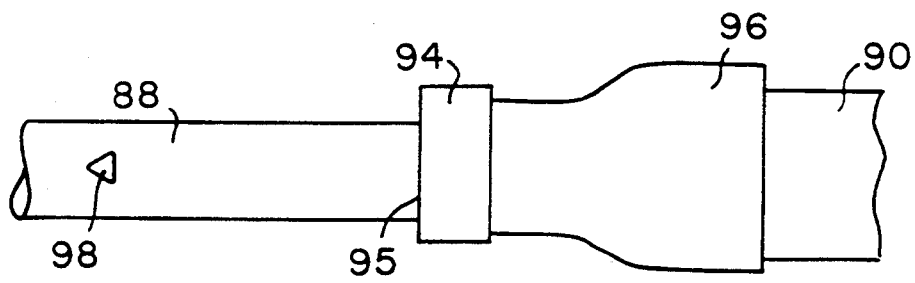
Figure 4B:
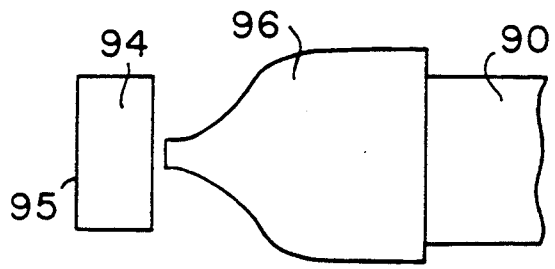

Referring to FIGS. 4–4b, the tip 96 may be fabricated of a compliant material, such as silicone tubing. The elasticity of the tubing causes the tip 96 to form inwardly around the catheter body 88, forming a seal to prevent body fluids from reaching the plug 94 (FIG. 4). When the sheath is withdrawn proximally over the plug, the tip 96 is stretched elastically over the plug and, distal of the plug, rebounds elastically to form a seal over stop 116 (discussed below), preventing any blood flow through the sheath and providing a stop that prevents the plug from moving any substantial distance proximally when the catheter is removed (FIG. 4a). When the catheter 88 is removed from the sheath, the tip 96 closes the end of the sheath, preventing flow of body fluids (FIG. 4b).

Figure 5:
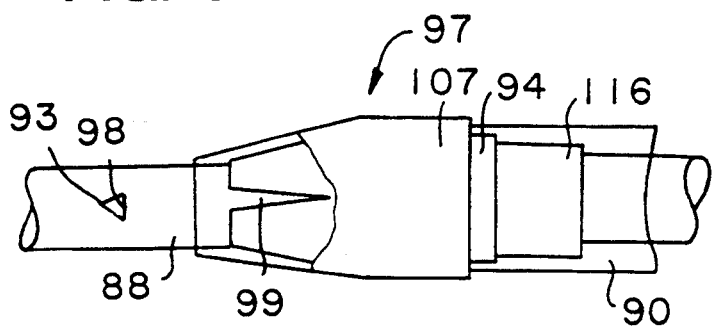
FIGS. 5-5b show an alternate tip for a protective sheath for use with the embodiment of FIG. 3.
Figure 5A:
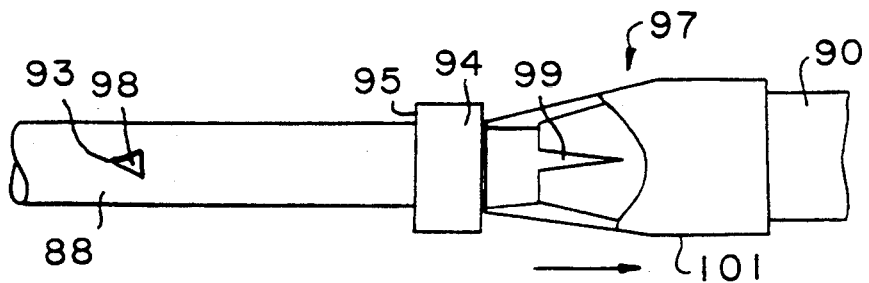
Figure 5B:
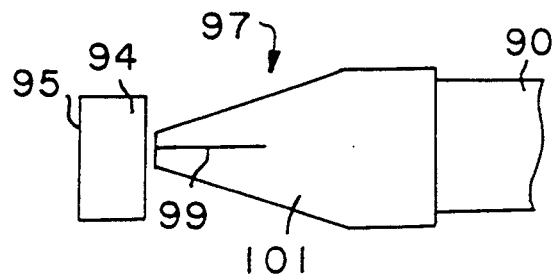

Referring to FIGS. 5–5b, in another embodiment, the tip 96 may be formed by providing a slice 99 longitudinally in the end of the sheath and providing an elastic material 101 such as silicon tubing to bias the end of the sheath closed. The tip 97 seals against the catheter 88 when present (FIG. 5), seals over the stop 116 (discussed below) when retracted (FIG. 5a), and closes the distal end of the sheath with the catheter removed (FIG. 5b).

Annular collagen plug 94 is located over catheter 88 and, during positioning in the access channel, held in a state of compression by protective sheath 90. Plug 94 is typically a cylinder having an inner diameter equal to that of catheter 88 and an outer diameter in a compressed state equal to the inner diameter of protective sheath 90. Plug 94 is fabricated of a single layer of a compressed matrix of hemostatic collagen, so while its mounted dimensions were as described, its unloaded diameter may be much larger. The unloaded size of plug 94 may be on the order of 30 French (10 mm) outer diameter. The internal diameter is formed by forcing the catheter 88 through the collagen matrix 94 when loading. The axial length of the plug is known and does not vary significantly after removal of the sheath or on exposure to blood. Plug 94 is preferably short, about 2 cm long, but may be of a different length generally equal to or shorter than the insertion site. Accordingly, the plug 94 typically weighs about 30–50 mg but may change with volume or hemostatic requirements. The distance from the distal end 95 of the plug to the distal part 93 of the port 98 is a known distance, $L_6$, about 1 cm.

A clear heat shrunk polymer tube is used to form stop 116. The stop is positioned on the catheter just proximal of collagen plug 94. Typically, stop 116 is located about 3 cm proximal the side port 98. This tube is made of a material such as teflon. The stop, formed by the ledge created by the end of the tube, stops plug 94 from distal motion when protective sheath 90 is initially withdrawn. The tube and hence the stop 116 typically has a thickness of 0.010 inch. The inner diameter of the tube is equal to the outer diameter of catheter 88, as the tube is securely fixed. An adhesive may be used to fix the tube upon catheter 88. The tube is typically about 1–2 cm long. A longer tube may be used to either aid fixation or to increase the strength of catheter 88. In other embodiments, a stopping mechanism in the form of a bump, hook, balloon or the like can be used to prevent proximal axial motion of the plug during sheath retraction. The stopping mechanism may be activated from the proximal end of the device to protrude from an otherwise uniform tubular catheter body.

Figure 6A:
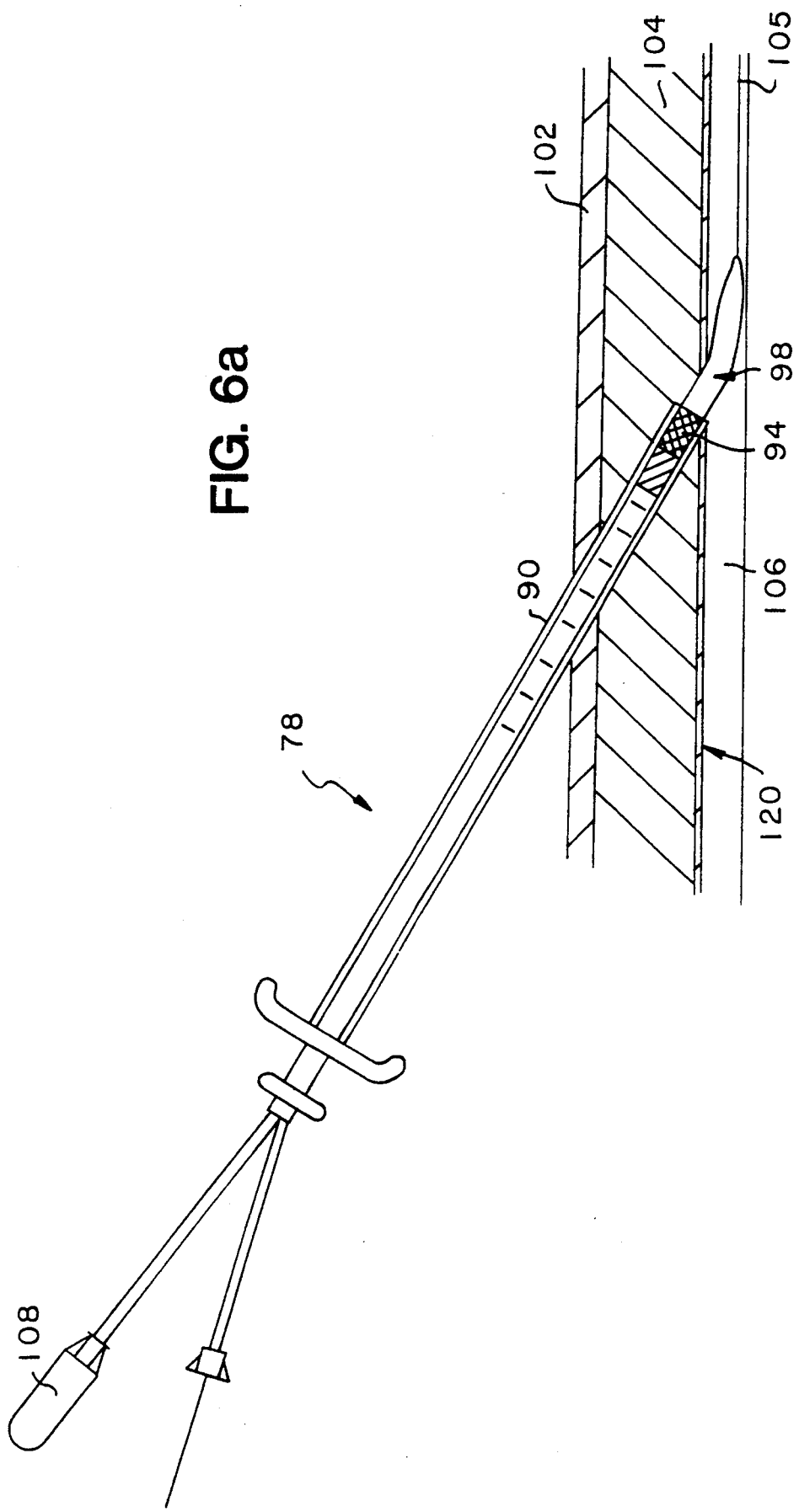
FIGS. 6-6d illustrate use of the device in FIG. 3.
Figure 6B:
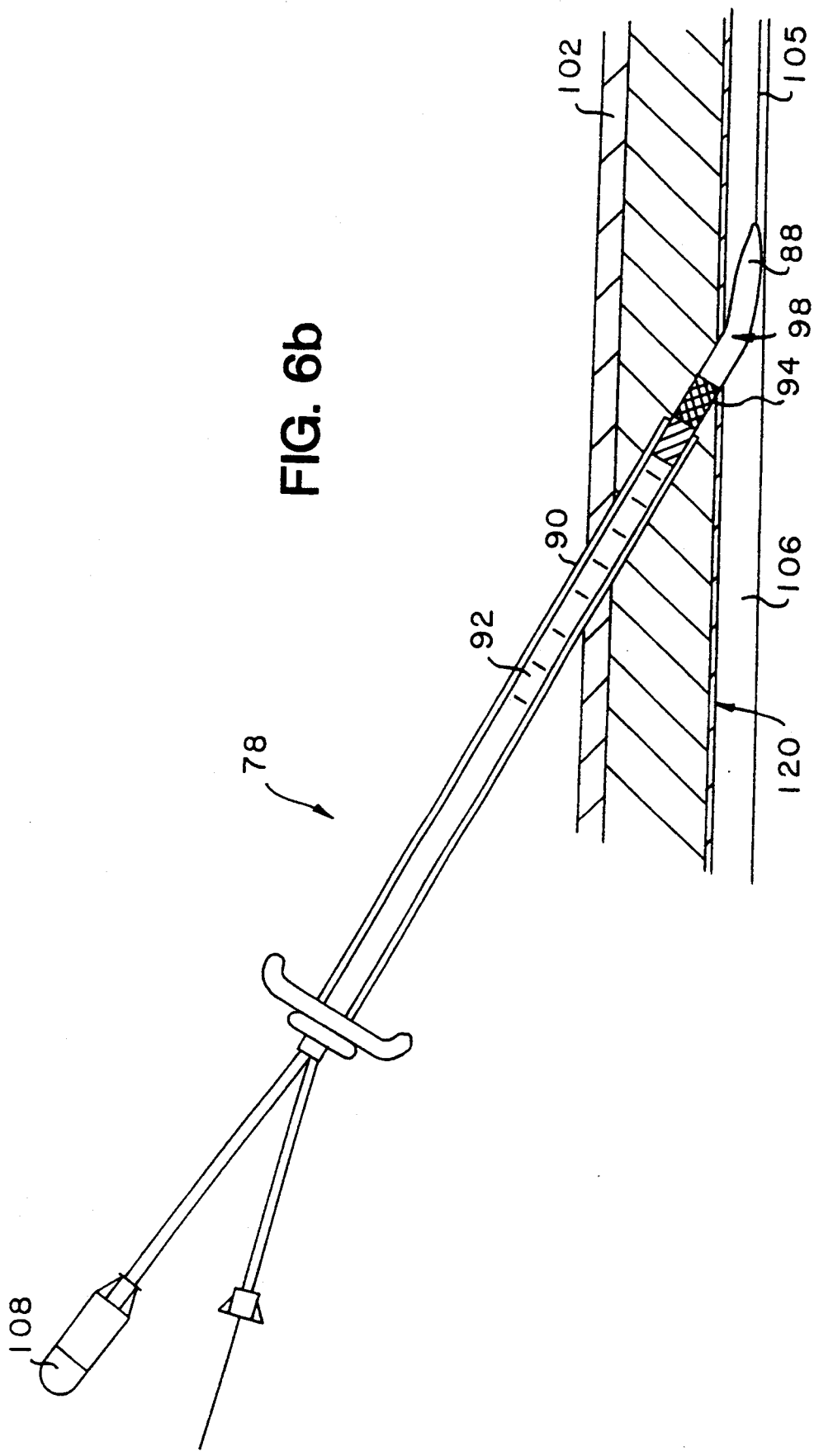
Figure 6C:
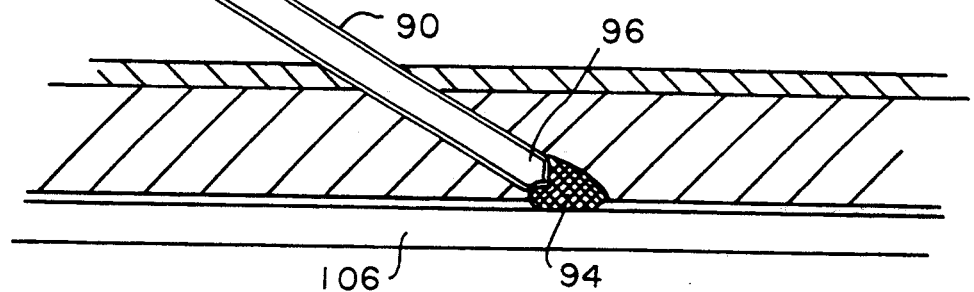
Figure 6D:
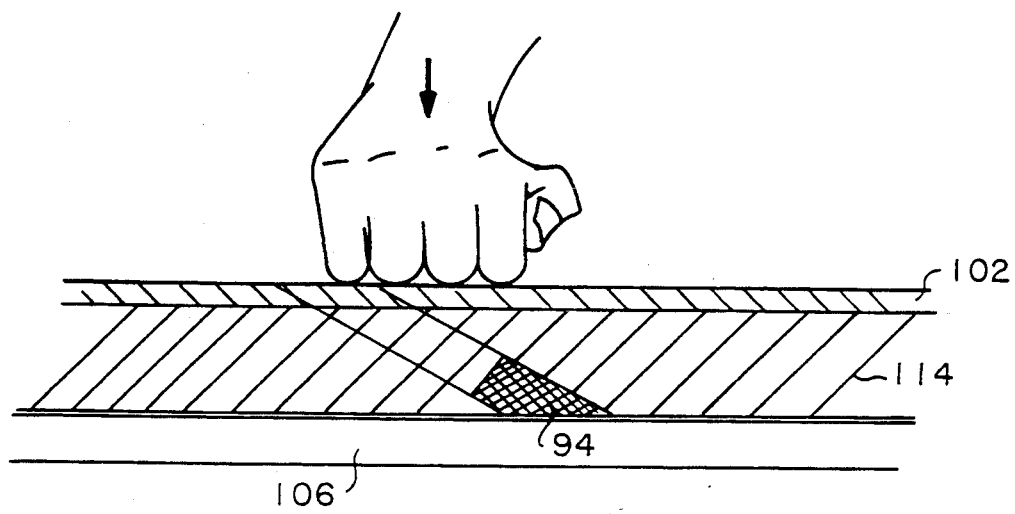

Referring to FIGS. 6–6d, the device 78 may be used as follows. The wound or access channel 118 is seen in FIG. 6 where skin 102 lies over subcutaneous tissue 104 (fat, fascia, muscle, etc.) which lies over blood vessel 106. Blood vessel 106 has a wall 120. Upon removal of a cardiovascular catheter or another medical device from the channel, a guidewire 105 (0.038 inch, 80 cm) is fed into the puncture to act as a guide for the device. When first inserted, side port 98 is located far within blood vessel 106. Blood pressure causes blood to flow through the side port 98, lumen 112, and into indicator 108. This initial depth of insertion assures that the side port extends into the blood vessel, as indicated by a blood flow response (no blood flow would mean that the side port has not entered the vessel). The device may be rotated to assure that the side port 98 is not blocked-off by the interior wall of the vessel lumen. As illustrated, the sheath 90 extends axially distally over the plug 94.

Referring to FIG. 6a, the device 78 is positioned so that the side port is adjacent the vessel wall. The device 78, with plug 94, is gradually pulled proximally out of blood vessel 106. As withdrawal occurs, side port 98 eventually will be located at the level of the vessel wall 120. Once all of side port 98 is external to vessel 106 and at the level of vessel wall 120, blood flow through the port will cease. This condition is indicated by indicator 108. The cessation of blood flow is evident at any level in the access site 118 external to vessel 106. It is therefore preferable to iteratively move the device back and forth into and out of the vessel 106 to assure the user that the exact level of vessel wall 120 has been reached without being excessively external to vessel 106.

Referring to FIG. 6b, the plug is positioned accurately adjacent the vessel wall and protective sheath 90 is withdrawn from over plug 94. Once the exact position has been reached where the side port 98 is located just superior to vessel wall 120, the measurement from skin level 102 to the vessel wall 120 is noted by observation of depth marks 92. As mentioned, plug 94 is located, $L_6$, 1 cm proximal to side port 98 (to provide room for tapered tip 96 to close and seal over the plug 94). For exact placement of the plug after positioning the side port, the device and plug 94 are then advanced distally 1 cm forward. The advancement to a depth of 1 cm is noted using marks 92 which are external to the body. The indicator 108 will once again indicate blood flow. With the plug correctly positioned, protective sheath 90 is withdrawn by pulling back on handles 86 until handle stop 84 is reached. Distally, tapered tip 96 will stretch open and around collagen plug 94. Plug stop 116 will prevent collagen plug 94 from moving proximally as protective sheath 90 is withdrawn. Once the length of plug 94 is transversed by tapered tip 96, the tip will then seal back around plug stop 116. The tip 97 of the sheath prevents the plug from moving as the catheter is withdrawn, as illustrated above in FIGS. 4a and 5a.

When exposed to blood, plug 94 will swell and begin to expand and seat itself inside the channel. Hemostasis begins as the plug 94 is exposed. The plug 94 works both mechanically and hemostatically. Mechanically it will wedge itself in position within tissue tract 118. Hemostatically, plug 94 works on an ionic level to attract blood platelets and decrease the hemostatis time. The plug may have mechanical or pharmaceutical properties selected for a particular application and may contain materials other than collagen.

Referring to FIG. 6c, the catheter 88 of the delivery device and the guidewire are quickly withdrawn from within protective sheath 90. After the catheter is withdrawn, tapered tip 96 closes down upon itself to prevent any blood flow through the lumen. As mentioned, protective sheath 90 also serves to help hold plug 94 in place as catheter 88 is withdrawn. Tapered tip 96, being of a smaller outer diameter than plug 94, will not allow plug 94 to move within access tract 118. Further, in cases where the sheath includes graduated marks, the mark adjacent the skin level is noted once the sheath is retracted. Should the plug move proximally during removal of the catheter, the plug can be accurately repositioned by pushing the sheath distally to the proper depth.

Referring to FIG. 6d, manual compression is applied. Manual compression will be applied over the access site 118 and plug 94 for a period of 5 min. This period may not be necessary in non-vascular applications or with various materials or pharmaceutical adaptations of the plug 94. Plug 94 being biodegradable will eventually be dissolved or remodeled by local cells.

Compression may initially be applied before removal of the protective sheath 90 to allow time for plug 94 to seat hemostatically. Blood pressure may be strong enough to loosen the plug. Protective sheath 90 is flexible enough to collapse under manual compression. Furthermore, protective sheath 90 is antithrombogenic enough not to promote clotting on its own. Within 1 to 2 min, protective sheath 90 may be withdrawn to allow the access site 118 to close upon itself. Protective sheath 90 may also be withdrawn immediately following removal of catheter 88 if the plug 94 appears secure.

Referring to FIG. 7, an embodiment providing automated sequential retraction of the sheath 90 and catheter 88 is illustrated. The device includes a housing 130 that serves as a handle and contains a drive mechanism 132, shown in the loaded position. The sheath 90 extends through a first spring 134 and is attached to a first collar 136. The catheter 88 extends through the sheath 90, through a second spring 138, and is attached to a second collar 140. The catheter may include a further extension 142 to the end of the device body to provide access to the catheter flow and guidewire lumens. The first spring is held in the compressed state by a rocker arm 144, which can pivot about pin 145, and the second spring held in the compressed state by the rocker arm 146, which can pivot about pin 147. Rocker arm 145 includes a firing button 148.

In operation, the physician finds the proper location for depositing the plug 94 using the port 98 and indicator 108 in the manner discussed above. To deposit the plug, the firing button 148 is actuated, causing the rocker arm 144 to pivot and release the collar 136, which causes the sheath to be retracted. The sheath is retracted a distance, $L_8$, preselected by the travel, $L_8'$, of collar 136, which positions the distal tip 97 of the sheath just proximal of the plug 94. Collar 136, near the end of its travel actuates rocker arm 146, which pivots to release the collar 140, causing the catheter to be retracted. The catheter is retracted a distance, $L_9$, preselected by the travel, $L_9'$, of collar 140 which positions the distal tip 148 of the catheter proximal of the plug 94 and within the sheath 90. The device is then removed from the access channel leaving the plug 94 at the proper position. Construction details and additional features for the drive mechanism, including components for arming the device and a safety mechanism, can be adapted from the drive mechanisms for biopsy needle devices disclosed in U.S. Ser. No. 07/583,080, filed Sep. 14, 1990 and U.S. Pat. No. 4,958,625. The entire contents of both of these cases is hereby incorporated by reference.

Still further embodiments are possible. In the embodiment of FIG. 1, the plug is inserted into the access channel following the location of the vessel wall using the delivery device. In the embodiment of FIG. 3, the sheath and plug are inserted simultaneously with the insertion of the delivery device and during location. In the former, the plug is left in place to biodegrade. In the latter a sheath is removed and the plug left in place to biodegrade. Referring to FIG. 8, in another embodiment, the sheath and plug are inserted following the location of the vessel wall and the sheath is then removed leaving the plug to degrade. In this case, the device 120 consists of a ruled side port delivery catheter 122 with a stop 124 formed by a tube heat shrunk or otherwise fixed to the catheter. The tube extends a distance, $L_7$, (2 cm, for example) proximal to the side port creating a stop ledge 125. A collagen plug 126 (2 cm in length for example) lines the inside of a clear (such as polyethylene, etc.) plastic sheath 128 at the distal portion of the tube. The clear plastic sheath is typically about 10 cm long and 13 F in diameter (sized per the medical procedure previously performed). The plug 126 is therefore initially located between the clear plastic sheath 128 and the tube 124 and has a compressed inner diameter equal to the outer diameter of the tube 124 (about 8.3 F, for example) and a compressed outer diameter equal to the inner diameter of the clear sheath 128, (about 12 F, for example). The sheath 128 may be beveled or tapered at the distal tip to aid during entry into the body tissues.

The plug 126 is deployed in the following manner. The plastic sheath 128 and plug 126 are initially positioned on the proximal end of the delivery device as shown. Following location of the artery wall using a side port 10, the sheath 128 is used to advance the collagen sponge forward. The sheath may have small ridges on the inside wall to engage and carry the collagen forward. The plug 126 fits between the sheath and the tube 124 during advancement. Once the proximal end of the plug 126 had passed beyond the ledge 125, the collagen expands sufficiently (either through relaxation or fluid absorption) to prevent axial movement in a reverse (proximal) direction. The sheath 128 is then withdrawn and the plug, stopped by the ledge 125, stays in its deployed position. The outer sheath is withdrawn from the body, followed by removal of the catheter 122 and the application of pressure at the site, if necessary.

Many other embodiments are possible. For example, other embodiments can be mechanized to allow automatic, trigger-type actuation of a sheath, the catheter, and even distal extension of the plug a known distance from the side port. For embodiments relying on blood flow indication, the flow through the side port can be collected to sample fluid before the hemostatic material is delivered. The side port can be used to deliver a radiopaque dye to ensure positioning or to indicate lumen patency after protective sheath deployment. The device may also include radiopaque markings for initial positioning or confirmation. A side port catheter not carrying hemostatic material can be used to measure channel depth for other reasons or hemostatic material may be deposited subsequently by other means.

Still other embodiments are possible. For example, the shape of the side port can be selected to provide a desired flow pattern as it crosses the vessel wall. The port may be triangular, arranged with the widest part (base) of the triangle perpendicular to the catheter axis and toward the distal end so that an abrupt cessation or onset of blood flow occurs when the base passes the vessel wall. Multiple side ports and flow lumen arrangements can be used. Two side ports may be positioned at different axial locations on the catheter, each communicating with a separate flow lumen. The presence of flow in one lumen and the absence of flow in the other lumen is indicative that the vessel wall is located between the two side ports. Other detectors that indicate flow or pressure might be used, such as pressure transducers or doppler effect detectors.

In other embodiments, rather than a side port through the wall of the flow lumen, the port accesses the flow lumen on the axis of the flow lumen. In one such embodiment, the port is proximal of the distal end of the catheter body a known distance, sufficient that the tissue on the walls of the access channel seal against the portions of the catheter distal of the side port to stop blood flow into the channel and port. The alignment marks and plug are arranged so the plug can be positioned to extend this distance beyond the port to an axial position adjacent the vessel wall. This embodiment may be constructed by attaching a piece of straight length tubing to a single (guidewire) lumen catheter and disposing an annular plug over the catheter and tube. In another embodiment of this type, the catheter may be configured to create the access channel prior to the operation. In this case, the distal end of the catheter is similar to a hollow needle, i.e. it is made of a hard material, such as metal, and sharpened to a point for puncturing the skin. A port is located at the distal end of the point and accesses a flow lumen through the device. When the point first punctures the vessel wall, blood flows through the port and the depth of the channel can be determined using markings on the side of the device. After the operation, the device can be repositioned in the channel to deliver a plug using depth markings on the plug as discussed, for example, with respect to FIG. 1, to properly position the plug adjacent to vessel wall according to the depth previously measured.

Systems can be dimensioned and configured for use in various body vessels through which there is fluid flow, particularly fluid flow under pressure, such as other vessels in the vascular system, e.g., veins, or other non-vascular vessels, e.g., the bile duct, hepatic duct, lymph duct, renal duct, cerebral spinal fluid conduit.

Other types of vessel wall locators that do not indicate fluid flow may also be used. A notch in the side wall of an otherwise constant diameter of the catheter body, not connected to a flow lumen, may be used to locate a vessel wall or other tissue interface by creating a vibration in the catheter body when the notch passed across the interface, e.g. edge of the vessel wall. An hourglass shaped catheter wall can be employed to indicate the location of the vessel wall by noting the resistance of the catheter to axial motion, with the location of the side wall being indicated by a decrease and an increase in resistance as the catheter is moved axially. An expandable foam material can be used on the catheter, that swells upon exposure to fluid in the vessel. The expanded material would create resistance as it is pulled across the vessel wall. The expansion of the material is not so great as to prevent the catheter from being withdrawn into the access channel. Other detectors, e.g. chemical or biodetectors, such as a detector of salts can be used. Detectors mentioned above that do not rely on fluid flow can be used to position material relative to the interface of different tissues. For example, the locators that detect the difference in texture or elasticity of different tissues by, e.g. transmitting a vibration, to detect the interface of tissues. Various systems are possible that detect a location in a channel, including systems not located on the wall of the member, may use the depth measurement schemes as described above.

In still further embodiments, rather than an annular plug positioned over a catheter body, the collagen is held in a hollow plastic sheath which is inserted, positioned, and removed, leaving the plug in the body. The collagen does not move outward with the sheath due to a positioner or stopping member. This positioner could be a plunger, small hook, or balloon, e.g., located behind the collagen, that holds the collagen axially in place during sheath removal. The positioner is removed thereafter. The catheter may have three parallel lumens including a guidewire lumen, a flow lumen to a side port, and a lumen containing the plug. An advantage of this system is a lower profile upon insertion.

In further embodiments, rather than providing marks on the plug, the insertion depth can be verified by a slidable ruler attached to the device, which is slid into contact with the skin of the patient and indicates the length of a plug that extends beyond the surface of the body. The ruler is preferably clear or its profile less than a complete cylinder (e.g. half-cylinder) to allow visualization of the plug that it is measuring. In the latter embodiment, the substance can be seen under the ruler in the areas not covered by the ruler.

In further embodiments, a slidable securing ring or a securing clamp positioner is provided which can be selectively fixed to a plug or a protective sheath at a desired distance from the distal end. The ring or clamp has a diameter significantly larger than that of the body puncture, thus preventing any portion of the sheath proximal of the ring or clamp from being advanced into tissue. During device positioning, the ring prevents advancement of the sheath beyond the depth that was indicated by the delivery device. In cases (e.g., FIG. 8) where a separate, non-biodegradable sheath is removed following deployment of the healing material, the clamp or ring can be provided on the sheath and the depth at which the sheath is stopped allows exact remote placement of the degradable, healing substance. The ring also stabilizes the device by preventing any further advancement once the site has been reached and the site is being manipulated, i.e., as the device is removed or manual compression is applied. The ring or clamp could also serve as a handle making it easier to push or pull the sheath. The ring may be secured in a manner such as twisting, similar to a Touhy-Borsch locking mechanism. A clamp could have a spring mechanism, deformable polymer or a locking mechanism to secure it in place and allow subsequent removal. Furthermore, the ring or clamp may have a ruler associated with it, extending proximally to aid an accurate placement of the clamp on the plug or sheath. The ring or clamp may be removed following satisfactory positioning of the body healing substance.

Figure 9:
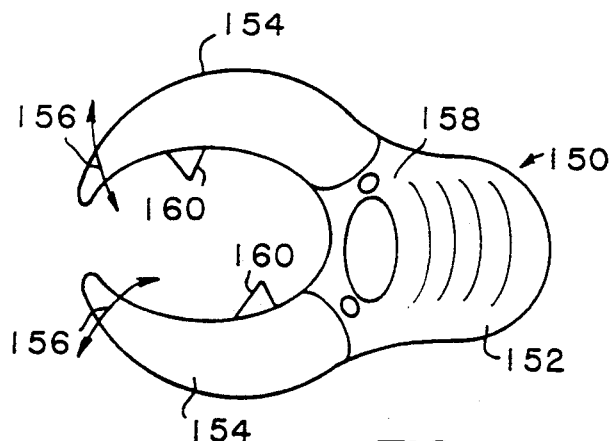
FIG. 9 is a top view of a clamp positioner according to the invention.

Referring to FIG. 9, a clamp-positioner 150 is shown for positioning a plug that also has the additional function of removing the excess plug material after positioning. The clamp 150 includes a relatively wide handle portion 152 and clamping arms 154. The clamping arms 154 can be controlled (arrows 156) to adjust the clamping pressure by a gear mechanism 158 in the handle portion 152. (Alternately, the arms may be spring biased inward or constructed of a deformable material.) The clamping arms further include blade members 160 for cutting the plug material.

Figures 10, 10A, 10B, 10C:
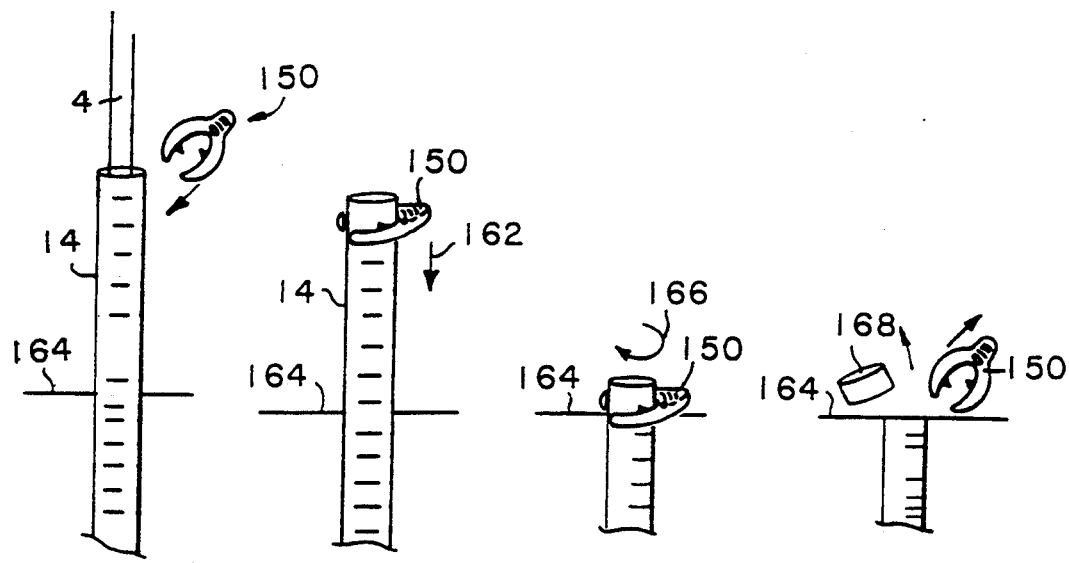
FIGS. 10-10c show the use of the clamp positioner in FIG. 9.

Referring to FIGS. 10–10c, in use, the device may be positioned on the plug at the axial location from the distal end corresponding to the depth of the access channel (particularly, FIGS. 10 and 10a). This depth is determined using a side port catheter, as discussed above, for example with respect to FIG. 1. The clamp is tightened so the blades 160 firmly grip or cut into the plug. The catheter may be removed or remain in the body. The plug 14 is then positioned (arrow 162) such that the handle portion of the plug is adjacent the skin 164 (FIG. 10b). Finally, the clamp is rotated (arrow 166) so the blades cut through the plug, to remove the excess portion that extends above the skin when the plug is properly positioned (FIGS. 10b and 10c).

Figure 11:
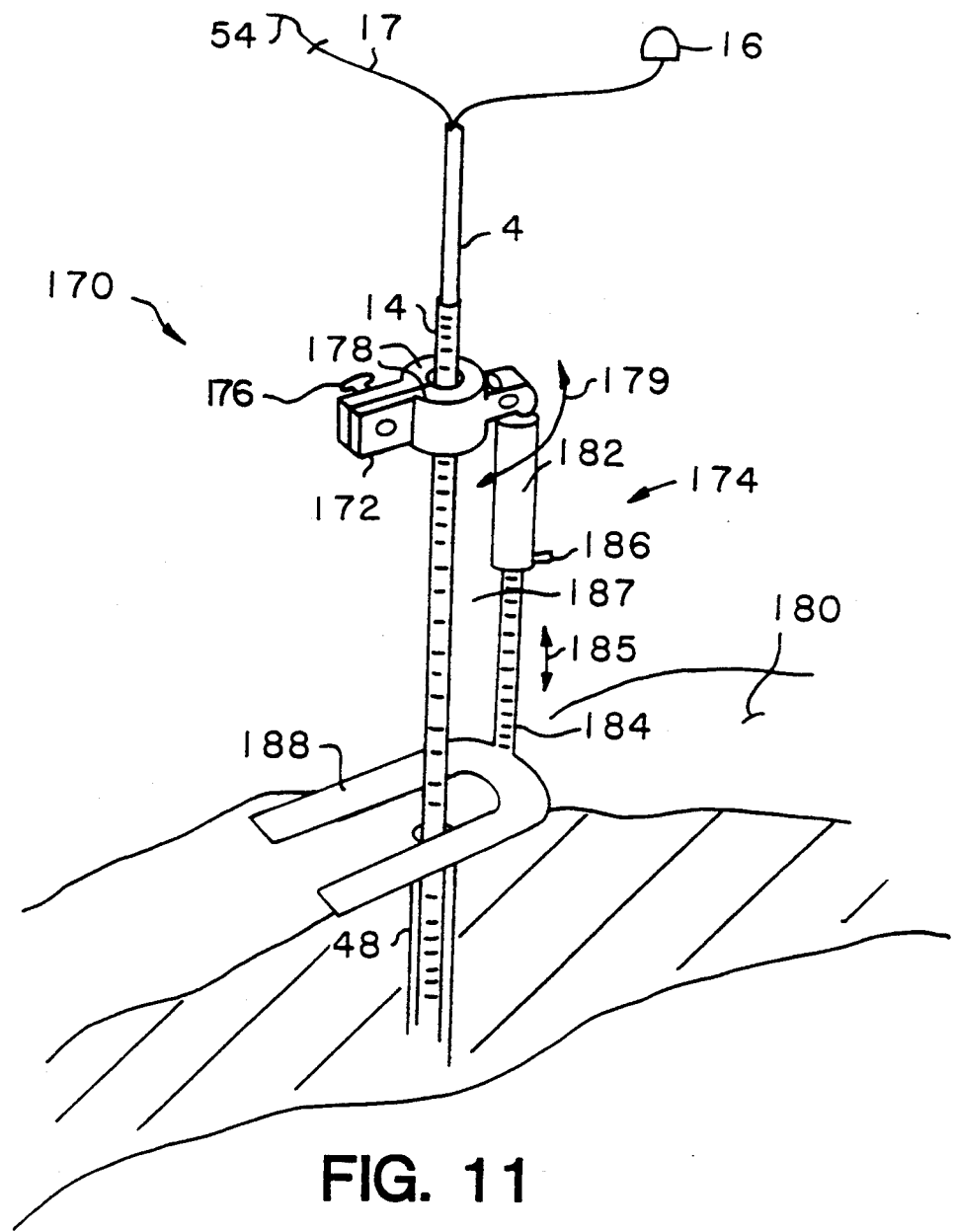
FIG. 11 is a perspective view of another clamp positioner.

Referring to FIG. 11, in another embodiment, a positioner 170 includes a clamping portion 172, that can be fixed to the plug 14, and an adjustable leg assembly 174. The clamping portion 172 includes an adjustment screw 176 to tighten clamp arms 178 around the plug to fix the axial position of the positioner with respect to the plug. The clamping arms are joined to the leg assembly at a pivot point so the leg assembly can be pivoted (arrow 179) away from the surface of the body 180 during initial positioning. The leg portion 174 includes an upper housing 182 which axially receives a lower adjustable leg 184 (arrow 185). The leg 184 can be fixed at a desired extended length with a screw assembly 186. The leg 184 includes a series of graduated marks 187 and extends to a foot 188 which is shaped to allow the catheter body 4 and plug 14 to pass into an access channel 48.

In use, the positioner 180 is clamped to proximal end of the plug 14 as shown, but with the leg assembly pivoted away from the body while the depth of the access channel is determined. Once determined, the leg assembly is adjusted so that the leg 184 extends to a length that will position the distal end of the plug adjacent the vessel wall when the foot rests on the body surface 180. The proper extension length is selected by observation of the alignment marks 187 on the adjustable foot portion 184, which indicate depth in correspondence with marks on the catheter body that measure the channel depth. The foot and the plug are then slid axially toward the body until the foot 188 rests on the body surface 180, thus positioning the distal end of the plug at the proper depth. The catheter body and guidewire can be removed from the channel, while the positioner stabilizes the plug against axial motion. Finally, the excess portion of the plug extending outside the body can be removed and the clamp removed from the excess portion for reuse. The clamp positioner can also be used to steady the device during positioning of the plug by resting the foot 188 on the surface 180 and allowing the leg 184 to freely extend and retract as the plug is positioned without using the marks 187 on the foot positioner 184.

Still other embodiments are within the following claims.

What is claimed is:

1. A device for treating an incision channel that extends through tissue and the wall of a body lumen, comprising:
   a member having a proximal portion that remains outside the body and an elongate distal portion that is introduced axially into said channel,
   a detector disposed on the side of said distal portion to detect an axial location along said channel,
   a healing promoting substance having a desired axial length, being carried by the exterior of said member, and being releasable from said member into the channel at a desired axial position relative to said location detected by said detector and,
   a healing promoting substance locator mark on the proximal portion of said member remaining outside the body at select axial distance from said detector based on the axial length of said healing promoting substance for locating said substance at said desired axial position in said channel when the detector is at the axial location detected by said detector.

2. The device of claim 1 wherein said detector is differentially responsive when exposed to the interior of said vessel and when exposed to the interior of said channel.

3. The device of claim 2 wherein said detector is sensitive to the flow of body fluid in said vessel.

4. The device of claim 3 wherein said detector includes a port in the wall of the generally tubular distal end portion so that said detector indicates when said port is exposed to the interior of said vessel by the flow of body fluid into said port and indicates when said port is exposed to the interior of said channel by the lack of flow of body fluid into said port.

5. The device of claim 4 further including a lumen extending proximally to the proximal portion of said member outside of said body and in fluid communication with said port.

6. The device of claim 5 wherein said lumen is sealed distal of said port.

7. The device of claim 6 wherein said lumen extends proximally to a visual indicator so the flow of body fluid through said port is indicated visually by flow at said visual indicator.

8. The device of claim 1 wherein said substance for promoting healing has a proximal end, distal end, and a known length therebetween, and said substance is positionable by alignment of said proximal end with said mark to position the distal end at a known axial distance with respect to said detector.

9. The device of claim 8 wherein said mark is located at a distance from said detector corresponding to the length of said substance so the distal end of said substance is adjacent said detector when the distal end of said substance is aligned with said mark.

10. The device of claim 1 including a series of additional marks on said member of known distances from said detector.

11. The device of claim 1 or 10 wherein said substance for promoting healing has a proximal end, distal end, and a known length therebetween and a series of marks indicating the distance from said distal end.

12. The device of claim 11 wherein said substance is slidably disposed on the exterior of said member.

13. The device of claim 12 wherein said substance is opaque, obscuring visual observation of portions of the member under said substance.

14. The device of claim 1 wherein said substance has a defined length greater than the depth of said access channel.

15. The device of claim 14 wherein said substance is axially moveable immediately after release from said member.

16. The device of claim 1 wherein said healing promoting substance is carried on the outer exposed surface of said tubular distal portion, and
said device further includes a sheath positioned over said substance during entry into said channel and removable from said position over said substance for releasing of said substance in said channel.

17. The device of claim 1 wherein said distal portion includes a relatively flexible tip, distal of said detector, for positioning inside said vessel.

18. The device of claim 1 wherein said distal portion tapers distally to smaller diameter.

19. The device of claim 1 wherein said member includes a lumen for delivering said device to the channel over a guidewire.

20. A system for treating an incision channel that extends through tissue and a blood vessel wall, comprising:
a member having a proximal portion that remains outside the body and an elongate, generally tubular distal portion that is introduced into and axially moveable within said channel,
a port in the wall of said generally tubular distal portion, a lumen in fluid communication with and sealed distal of said port and extending proximally to the proximal portion of said member outside the body,
a visual indicator in fluid communication with said lumen, the flow of blood through said port and to said indicator indicating when said port is exposed to said vessel and the lack of flow of blood through said port to said indicator indicating that said port is exposed to the interior of said channel, such that the port can be positioned near the vessel wall by moving said member axially,
a body-degradable hemostatic substance of desired axial length, slideably guideable along the exterior of said member for release into said channel at a desired axial position relative to said vessel wall and,
a mark on the portion of said member that remains outside the body at select axial distance from said detector based on the length of said hemostatic substance for locating the substance at the desired axial position along the channel when the detector is near the vessel wall.

21. The sytem of claim 20 wherein said member includes a lumen for delivering said device to the channel over a guidewire.

22. The system of claim 21 wherein the member includes a relatively flexible distal tip, distal of said port, for positioning inside the vessel.

23. The system of any one of claims 20, 21 or 22 wherein said hemostatic substance has a proximal end, distal end, and a known length therebetewen, and said substance is positionable by alignment of said distal end with said mark.

24. The system of claim 23 wherein said mark is located at a distance from the port corresponding to the length of said substance so that the distal end of said substance is adjacent said port when the proximal end of said substance is aligned with said mark.

25. The system of claim 24 further including a ruler for measuring the length of healing promoting substance extending proximally of said channel.

26. The device of any one of claims 1, 8, 17, 24, or 19 sized and constructed for treating an incision channel to a blood vessel.

* * * * *

UNITED STATES PATENT AND TRADEMARK OFFICE
CERTIFICATE OF CORRECTION

PATENT NO.   : 5,431,639

DATED        : July 11, 1995

INVENTOR(S)  : William J. Shaw

It is certified that error appears in the above-identified patent and that said Letters Patent is hereby corrected as shown below:

Col. 21, line 25, before "distal" insert --a--.

Col. 22, line 48, "therebetewen" should be --therebetween--. (our error)

Col. 22, line 59, delete "24".

Signed and Sealed this

Thirteenth Day of August, 1996

BRUCE LEHMAN

*Attest:*

*Attesting Officer*      *Commissioner of Patents and Trademarks*